United States Patent
Gasser et al.

(10) Patent No.: US 12,020,822 B2
(45) Date of Patent: Jun. 25, 2024

(54) IMAGING WAYPOINTS FOR RADIATION TREATMENT

(71) Applicant: SIEMENS HEALTHINEERS INTERNATIONAL AG, Steinhausen (CH)

(72) Inventors: Dominique Oliver Gasser, Oberrohrdorf (CH); Janne I. Nord, Espoo (FI); Joakim Olavi Pyyry, Helsinki (FI)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 920 days.

(21) Appl. No.: 16/112,736

(22) Filed: Aug. 26, 2018

(65) Prior Publication Data

US 2020/0066409 A1    Feb. 27, 2020

(51) Int. Cl.
| | |
|---|---|
| G16H 20/40 | (2018.01) |
| A61N 5/10 | (2006.01) |
| G16H 50/50 | (2018.01) |
| G06T 11/20 | (2006.01) |

(52) U.S. Cl.
CPC ............. *G16H 50/50* (2018.01); *A61N 5/103* (2013.01); *A61N 5/1049* (2013.01); *G16H 20/40* (2018.01); *G06T 11/206* (2013.01)

(58) Field of Classification Search
CPC ........ G16H 50/50; G16H 20/40; G16H 40/63; G06F 30/20; G06T 11/206; G06T 2200/24; G06T 2210/21; G06T 2210/41; A61N 2005/1061; A61N 5/103; A61N 5/1049; A61N 5/10; A61N 5/1043; A61B 6/54; A61B 6/0407; A61B 6/102
See application file for complete search history.

(56) References Cited

U.S. PATENT DOCUMENTS

| | | | | |
|---|---|---|---|---|
| 7,574,251 B2 * | 8/2009 | Lu | ........................ | A61N 5/1031 600/411 |
| 7,657,304 B2 * | 2/2010 | Mansfield | ............ | A61B 6/4429 378/65 |
| 7,810,996 B1 * | 10/2010 | Giphart | .................. | A61B 6/541 378/207 |

(Continued)

OTHER PUBLICATIONS

T O'Brien, Ricky, et al. "Respiratory motion guided four dimensional cone beam computed tomography: encompassing irregular breathing." Physics in Medicine & Biology 59.3 (2014): 579. (Year: 2014).*

(Continued)

*Primary Examiner* — Boris Gorney
*Assistant Examiner* — David A Hopkins
(74) *Attorney, Agent, or Firm* — Duane Morris LLP

(57) ABSTRACT

An apparatus for treatment planning and/or treatment setup includes: a simulator configured to obtain a first model representing a first component of a medical system, and virtually move the first model to simulate a movement of the first component of the medical system; an analyzer configured to determine imaging waypoints during a treatment process based on the virtual movement of the first model; and a graphic generator configured to generate a graphic based on the determined imaging waypoints.

22 Claims, 18 Drawing Sheets

(56) References Cited

U.S. PATENT DOCUMENTS

| | | | |
|---|---|---|---|
| 2004/0138557 A1* | 7/2004 | Le | A61B 5/7285 600/428 |
| 2005/0228255 A1* | 10/2005 | Saracen | A61B 6/0487 600/407 |
| 2009/0074151 A1 | 3/2009 | Henderson et al. | |
| 2009/0110238 A1* | 4/2009 | Li | A61N 5/103 382/103 |
| 2009/0180666 A1* | 7/2009 | Sheng | A61B 6/00 382/128 |
| 2010/0054410 A1* | 3/2010 | Nord | A61N 5/1031 378/65 |
| 2011/0080990 A1* | 4/2011 | Filiberti | G16H 20/40 378/65 |
| 2011/0210261 A1* | 9/2011 | Maurer, Jr. | A61B 6/025 250/393 |
| 2012/0109608 A1* | 5/2012 | Core | G16H 50/50 703/6 |
| 2012/0136194 A1* | 5/2012 | Zhang | A61N 5/103 600/1 |
| 2013/0142310 A1* | 6/2013 | Fahimian | A61N 5/103 378/65 |
| 2013/0336449 A1* | 12/2013 | Tanabe | A61N 5/1067 378/62 |
| 2014/0192952 A1* | 7/2014 | Keall | A61B 6/4085 378/8 |
| 2014/0321615 A1* | 10/2014 | Carlsson | A61N 5/1049 378/62 |
| 2015/0265219 A1* | 9/2015 | Feiweier | A61B 5/055 600/407 |
| 2015/0305692 A1* | 10/2015 | Klahr | A61N 5/1039 600/425 |
| 2016/0023019 A1* | 1/2016 | Filiberti | A61N 5/1045 600/1 |
| 2016/0228728 A1* | 8/2016 | Dempsey | A61N 5/1071 |
| 2017/0220709 A1* | 8/2017 | Wan | G06F 30/20 |
| 2017/0281975 A1* | 10/2017 | Filiberti | A61N 5/1048 |
| 2018/0038930 A1* | 2/2018 | Kroell | G01R 33/543 |
| 2018/0056091 A1* | 3/2018 | Jordan | A61B 6/032 |
| 2018/0160994 A1* | 6/2018 | Harrington | A61B 6/5217 |
| 2018/0192978 A1* | 7/2018 | Naylor | A61N 5/1067 |
| 2019/0000407 A1* | 1/2019 | Muller | A61B 6/505 |
| 2019/0329073 A1* | 10/2019 | Meltsner | A61N 5/1048 |
| 2019/0380666 A1* | 12/2019 | Sheng | A61B 6/4482 |
| 2020/0041596 A1* | 2/2020 | Gui | G06N 3/045 |
| 2021/0145372 A1* | 5/2021 | Berlinger | A61N 5/1049 |

OTHER PUBLICATIONS

Ren, Lei, You Zhang, and Fang-Fang Yin. "A limited-angle intrafraction verification (Live) system for radiation therapy." Medical physics 41.2 (2014): 020701. (Year: 2014).*

T O'Brien, Ricky, Benjamin J. Cooper, and Paul J. Keall. "Optimizing 4D cone beam computed tomography acquisition by varying the gantry velocity and projection time interval." Physics in Medicine & Biology 58.6 (2013): 1705. (Year: 2013).*

Bernatowicz, K., et al. "Quantifying the impact of respiratory-gated 4D CT acquisition on thoracic image quality: A digital phantom study." Medical physics 42.1 (2015): 324-334. (Year: 2015).*

D D'Souza, Warren, Shahid A. Naqvi, and X. Yu Cedric. "Real-time intra-fraction-motion tracking using the treatment couch: a feasibility study." Physics in Medicine & Biology 50.17 (2005): 4021. (Year: 2005).*

Hunt, Margie A., et al. "Simultaneous MV-kV imaging for intrafractional motion management during volumetric-modulated arc therapy delivery." Journal of applied clinical medical physics 17.2 (2016): 473-486. (Year: 2016).*

Keall, Paul J., et al. "Real-time 3D image guidance using a standard LINAC: measured motion, accuracy, and precision of the first prospective clinical trial of kilovoltage intrafraction monitoring-guided gating for prostate cancer radiation therapy.", 2016 (Year: 2016).*

Li, Guang, et al. "Clinical assessment of 2D/3D registration accuracy in 4 major anatomic sites using on-board 2D kilovoltage images for 6D patient setup." Technology in cancer research & treatment 14.3 (2015): 305-314. (Year: 2015).*

Mao, Weihua, et al. "A fiducial detection algorithm for real-time image guided IMRT based on simultaneous MV and kV imaging." Medical physics 35.8 (2008): 3554-3564. (Year: 2008).*

T O'Brien, Ricky, et al. "Reducing 4DCBCT imaging time and dose: the first implementation of variable gantry speed 4DCBCT on a linear accelerator." Physics in Medicine & Biology 62.11 (2017): 4300. (Year: 2017).*

Ostyn, Mark, Siyong Kim, and Woon-Hong Yeo. "A simulation study of a radiofrequency localization system for tracking patient motion in radiotherapy." Sensors 16.4 (2016): 534. (Year: 2016).*

Qiu, Peng, et al. "Inferential modeling and predictive feedback control in real-time motion compensation using the treatment couch during radiotherapy." Physics in Medicine & Biology 52.19 (2007): 5831. (Year: 2007).*

Stevens, M. Tynan R., Dave D. Parsons, and James L. Robar. "Continuous monitoring of prostate position using stereoscopic and monoscopic kV image guidance." Medical physics 43.5 (2016): 2558-2568. (Year: 2016).*

Sundar, Hari, et al. "Automatic image-based cardiac and respiratory cycle synchronization and gating of image sequences." International Conference on Medical Image Computing and Computer-Assisted Intervention. Springer, Berlin, Heidelberg, 2009. (Year: 2009).*

Victoria, Y. Yu, et al. "A prospective 4π radiation therapy clinical study in recurrent high-grade glioma patients." International Journal of Radiation Oncology* Biology* Physics 101.1 (2018): 144-151. (Year: 2018).*

Zhang, Pengpeng, et al. "Intrafractional 3D localization using kilovoltage digital tomosynthesis for sliding-window intensity modulated radiation therapy." Physics in Medicine & Biology 60.17 (2015): N335. (Year: 2015).*

Cardan, Rex A., Richard A. Popple, and John Fiveash. "A priori patient-specific collision avoidance in radiotherapy using consumer grade depth cameras." Medical physics 44.7 (2017): 3430-3436. (Year: 2017).*

Hua, Chiaho, et al. "A practical approach to prevent gantry-couch collision for linac-based radiosurgery." Medical Physics 31.7 (2004): 2128-2134. (Year: 2004).*

Mao, Weihua, Louis Lee, and Lei Xing. "Development of a QA phantom and automated analysis tool for geometric quality assurance of on-board MV and kV x-ray imaging systems." Medical physics 35.4 (2008): 1497-1506. (Year: 2008).*

Rodriguez, "Experimental Validation of a Collision Avoidance Software in Radiation Therapy", PhD Dissertation from Georgia Institute of Technology, Dec. 2017 (Year: 2017).*

Zheng, Dandan, et al. "A protocol to extend the longitudinal coverage of on-board cone-beam CT." Journal of applied clinical medical physics 13.4 (2012): 141-151. See the abstract and pp. 142-143 (Year: 2012).*

Yu, Victoria Y., et al. "The development and verification of a highly accurate collision prediction model for automated noncoplanar plan delivery." Medical physics 42.11 (2015): 6457-6467. See the abstract and pp. 6457-6460 (Year: 2015).*

Sheng, Ke. Concurrent image and dose reconstruction for image guided radiation therapy. The University of Wisconsin-Madison, 2005. PhD Dissertation. See pp. 1-2, and chapter 5 starting on p. 94. (Year: 2005).*

Li, Tuotuo, Jason Geng, and Shidong Li. "Performance assessment of 3D surface imaging technique for medical imaging applications." Emerging Digital Micromirror Device Based Systems and Applications V. vol. 8618. SPIE, 2013. See the abstract and p. 6 (Year: 2013).*

Chao, Max M., et al. "Image display for collision avoidance of radiation therapy: treatment planning." Journal of Digital Imaging 14.4 (2001): 186. See the abstract and pp. 186-187 and 189-191. (Year: 2001).*

European Search Report dated Jan. 3, 2020 for corresponding EP Application No. 19250010.6.

* cited by examiner

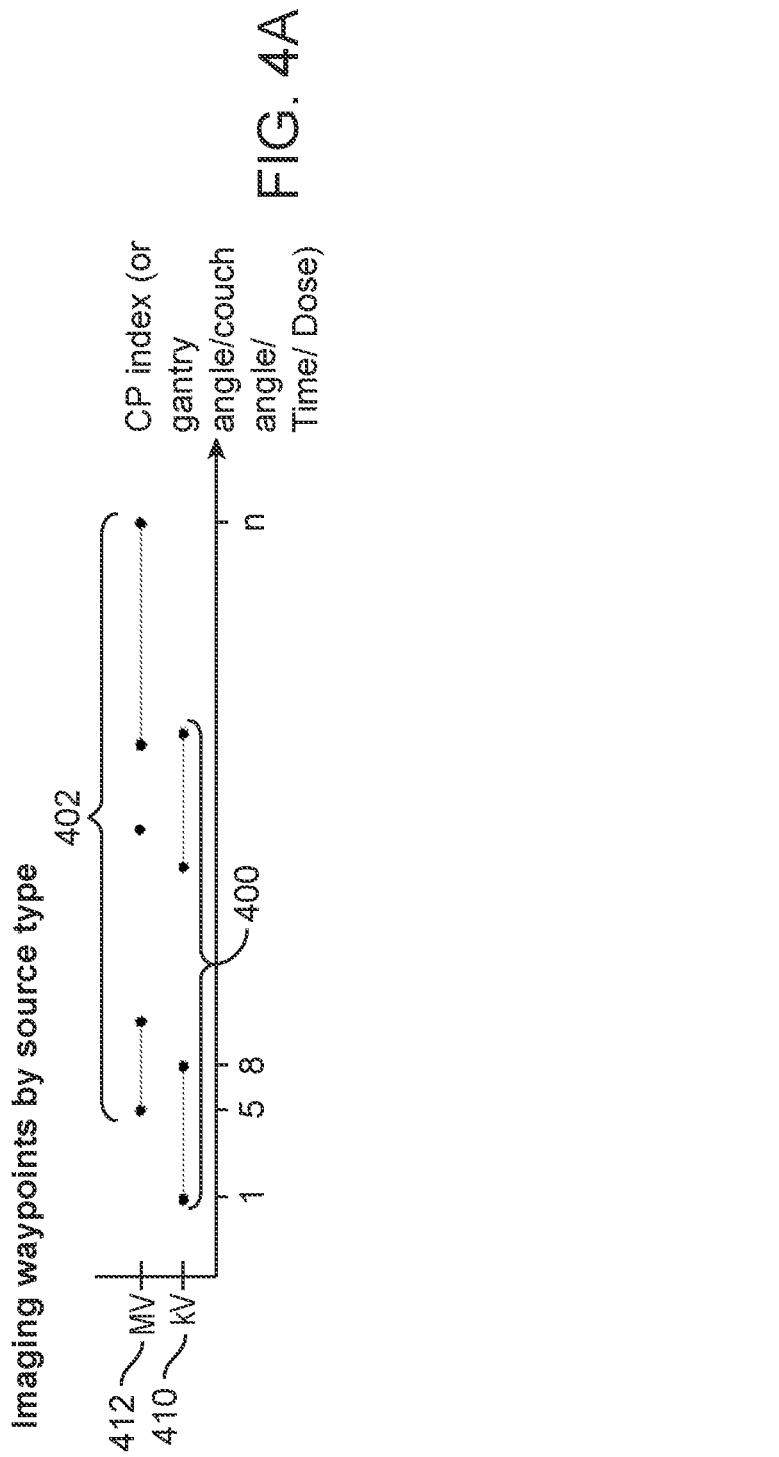

ated at a CT machine. Based on this "patient and couch outline" and a model of the treatment machine, a planning system then determines possible gantry and couch geometries that allow treatment only, imaging only, or both treatment and imaging. In the case where the "patient and couch outline" is not available for planning (e.g., if there is no surface scanner), then a user interface may be provided to a user to allow the user to select default patient surfaces of variable sizes for the planning process. In some cases, the input for the size selection may be a CT scan performed by the CT machine.
IMAGING WAYPOINTS FOR RADIATION TREATMENT

FIELD

The field of the application relates to radiation treatment, and more particularly, to systems and methods for determining radiation treatment plan while considering imaging options.

BACKGROUND

One of the main risks of radiation therapy treatment is collision of the treatment machine with the patient. Therefore, one has been very conservative when allowing other than 0 degree couch rotations with gantry rotations (non-coplanar treatments). With more complex trajectories and compact dose distributions in treatments like stereotactic radiosurgery (SRS) and stereotactic body radiation therapy (SBRT), one must allow for more safety critical angle combinations (of couch and gantry), with reduced machine to patient clearances. In addition, more setup verification X-ray imaging may be required, since there are more couch movements, which could potentially affect tumor position. With new treatment techniques, the dose gradients around the planning volume are steeper, so that accurate monitoring of tumor position is more important. This means that image verification during treatment becomes more important as very high doses may be applied in a short time.

If the entire treatment process is automated, imaging verification and treatment delivery are combined to a sequence of machine movements involving couch, gantry and imaging system. Doing so, the imaging system also becomes a part of the safety critical components, as during such an image verification process the imager and source arms need to deploy to acquire the image and to retract after image acquisition.

Currently, there is no way to define an amount of imaging that is possible during treatment. There is also no way to determine imaging waypoints for a complete treatment process, to display them, and to select imaging procedures from them.

Hence an improved mechanism to define the amount of imaging, to display the possible imaging options and to select the effective imaging is needed.

SUMMARY

In accordance with some embodiments, an apparatus is provided to determine imaging waypoints, which represent those points in time where imaging is possible. In some cases, the apparatus may include a collision prediction system, and may use a predefined, calculated, or user selectable amount of imaging, to define the amount of possible imaging procedures during treatment delivery process.

In one implementation, a surface scanner is first used to scan a patient's surface (which may also include setup aids and the patient support). The surface scanner may be implemented at a CT machine. Based on this "patient and couch outline" and a model of the treatment machine, a planning system then determines possible gantry and couch geometries that allow treatment only, imaging only, or both treatment and imaging. In the case where the "patient and couch outline" is not available for planning (e.g., if there is no surface scanner), then a user interface may be provided to a user to allow the user to select default patient surfaces of variable sizes for the planning process. In some cases, the input for the size selection may be a CT scan performed by the CT machine.

Next, the user (planner) selects via a user interface, or the apparatus suggests, a desired amount of imaging to be performed during the treatment process. For example, available options may include (1) no imaging at all (treatment only), (2) imaging during the entire treatment beam delivery (full imaging coverage), (3) treatment with partial imaging—in parallel to each other and/or sequentially, and (4) imaging only without treatment delivery. The user interface may allow a user to select an amount of imaging (e.g., percentage coverage), or the apparatus may suggest an amount of imaging, for trajectory calculation and dose distribution calculation. The apparatus may also allow (1) types of imaging source(s) (e.g., kV source, MV source, etc.), and (2) types of image acquisition (e.g., single image, paired images, continuous imaging, CBCT imaging, triggered imaging, etc.), for trajectory calculation and dose distribution calculation, to be defined via the user interface. Furthermore, in some cases, the user interface may allow the user to input one or more parameters (e.g., imaging geometry (such as source-to-imager distance, imaging distance, etc.), amount of imaging, machine geometry, etc.) for determining the imaging waypoints.

The apparatus then calculates all machine paths using a collision prediction system based on the selected amount of imaging in order to determine imaging waypoints. Optionally or additionally, the apparatus may provide a graphic via the user interface for visualization dose distributions based on the calculated paths. If desired, the apparatus may calculate new dose distribution.

Alternatively, the apparatus may calculate multiple different machine paths using the collision prediction system based on a selection of the imaging options and acquisition types to determine the imaging waypoints, and present the multiple different machine paths and imaging waypoints (and optionally together with the corresponding dose distributions) in the user interface. The user may then select the best option using the user interface.

The user interface may also allow a user to define a purpose of the imaging. For example, the user may define a type of verification to be performed after image acquisition (e.g., correct patient position, verify patient position, or no verification at all—i.e., image acquisition for bookkeeping).

The slot(s) or temporal point(s) where imaging can be done is referred as "imaging waypoint(s)". An imaging waypoint may be an instantaneous opportunity to acquire images, or a time slot where multiple images can be acquired over a longer period of time. Imaging waypoints may be for imaging that is to be executed in parallel or sequentially to treatment beam delivery.

After the imaging waypoints are presented to the user at the user interface, the user may use the user interface to select a subset of the imaging waypoints for imaging. Unselected imaging waypoints are available at a later stage when needed. The user interface may also allow a user to deselect a subset of the imaging waypoints.

During planning, the user interface provided by the apparatus may present a number of information to the user. For example, in addition to all possible imaging waypoints, the user interface may also present (1) imaging source types and/or (2) image acquisition types, for visualization. This may be done through a timeline, dose, or machine dependent graphic. The user interface would also allow the user to see at which machine positions no images can be taken. The user interface may also present graphics to inform the user about the dose distribution for a selected amount of imaging. In addition, the user interface may present trajectories for the machine (and optionally with dose distributions) for different amounts and/or types of imaging.

In some embodiments, the user interface may allow the user to modify one or more parameters (e.g., imaging geometry (such as source-to-imager distance, imaging distance, etc.), amount of imaging, machine geometry, etc.). In such cases, after the parameter(s) is modified, the apparatus will recalculate the imaging waypoints based on the modified parameter(s), and will present new graphics to present the recalculated imaging waypoints. In some cases, if the user is not satisfied with the current amount and types of imaging, the user can select an alternative amount of imaging presented by the apparatus, yielding a different (e.g., better) trajectory and dose distribution.

During treatment or on the day of treatment, the imaging waypoints selected during treatment planning for image acquisition are available for imaging. Through the user interface, the user can see all possible imaging waypoints determined previously during treatment planning. From the presentation, the user would also see at which machine positions no images can be taken. In some cases, the user interface may also present all combination of source types and acquisition types in a timeline with respect to the imaging waypoints. Also, the user interface may present dose, beam trajectories, and/or machine geometries, with respect to the imaging waypoints. If desired, unused imaging waypoints may be enabled, or previously enabled imaging waypoints may be disabled at the treatment console. In some cases, the user interface may also allow the user to add imaging waypoints, and/or to remove imaging waypoints during treatment planning and/or during treatment.

An apparatus for treatment planning and/or treatment setup includes: a simulator configured to obtain a first model representing a first component of a medical system, and virtually move the first model to simulate a movement of the first component of the medical system; an analyzer configured to determine imaging waypoints (at which imaging is possible during a treatment process) based on the virtual movement of the first model; and a graphic generator configured to generate a graphic based on the determined imaging waypoints.

Optionally, the simulator is also configured to obtain a second model representing a patient support, and virtually move the second model to simulate a movement of the patient support.

Optionally, the simulator is also configured to obtain a surface model of a patient, and virtually move the surface model to simulate a movement of the patient due to a movement of a patient support Optionally, the analyzer comprises a collision analyzer.

Optionally, the apparatus further includes an input for receiving a user-defined amount of imaging coverage, wherein the analyzer is configured to determine the imaging waypoints based on the user-defined amount of imaging coverage.

Optionally, the imaging waypoints comprise a first set of imaging waypoints and a second set of imaging waypoints, and wherein the analyzer is configured to determine the first set of imaging waypoints for a first type of imaging, and to determine the second set of imaging waypoints for a second type of imaging.

Optionally, the first type of imaging comprises kV-imaging, and the second type of imaging comprises MV-imaging.

Optionally, the first type of imaging is room-based imaging, gantry-based imaging, or couch-based imaging.

Optionally, the first type of imaging requires a component of a treatment machine to move away from a certain position Optionally, the first type of imaging does not require the component of the treatment machine to move away from the certain position.

Optionally, the graphic generator is configured to generate the graphic to present the imaging waypoints as control point indices.

Optionally, the control point indices comprise or represent: gantry angles, couch angles, time points, or doses.

Optionally, the imaging waypoints are arranged in the graphic as a function of imaging distance.

Optionally, the imaging distance and the imaging waypoints define one or more two-dimensional areas in the graphic.

Optionally, the imaging waypoints are arranged in the graphic as a function of angle offset between two kV-imager positions of a same imager or of different respective imagers.

Optionally, the analyzer is also configured to determine gantry angle of a gantry associated with a treatment energy source as a function of control point index.

Optionally, the graphic generator is also configured to provide a diagram indicating the gantry angle as the function of the control point index.

Optionally, the analyzer is also configured to determine couch angle of a couch as a function of control point index.

Optionally, the graphic generator is also configured to provide a diagram indicating both the gantry angle and the couch angle as the function of the control point index.

Optionally, the graphic generator is also configured to provide a diagram indicating how the couch angle varies in relation to the gantry angle.

Optionally, the graphic is a part of a user interface configured to allow a user to select one or more imaging arrangement(s) for a treatment plan.

A method for treatment planning and/or treatment setup includes: obtaining a first model representing a first component of a medical system; virtually moving the first model to simulate a movement of the first component of the medical system; determining, by an analyzer, imaging waypoints (at which imaging is possible during a treatment process) based on the virtual movement of the first model; and generating, by a graphic generator, a graphic based on the determined imaging waypoints.

A product having a non-transitory medium storing a set of instructions, an execution of which by a processing unit causes a method to be performed during treatment planning and/or treatment setup, the method includes: obtaining a first model representing a first component of a medical system; virtually moving the first model to simulate a movement of the first component of the medical system; determining, by an analyzer, imaging waypoints (at which imaging is possible during a treatment process) based on the virtual movement of the first model; and generating, by a graphic generator, a graphic based on the determined imaging waypoints.

Other and further aspects and features will be evident from reading the following detailed description.

DESCRIPTION OF THE DRAWINGS

The drawings illustrate the design and utility of some embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

FIGS. 4A-4B illustrate imaging waypoints by source type.

DETAILED DESCRIPTION

Figure 1:
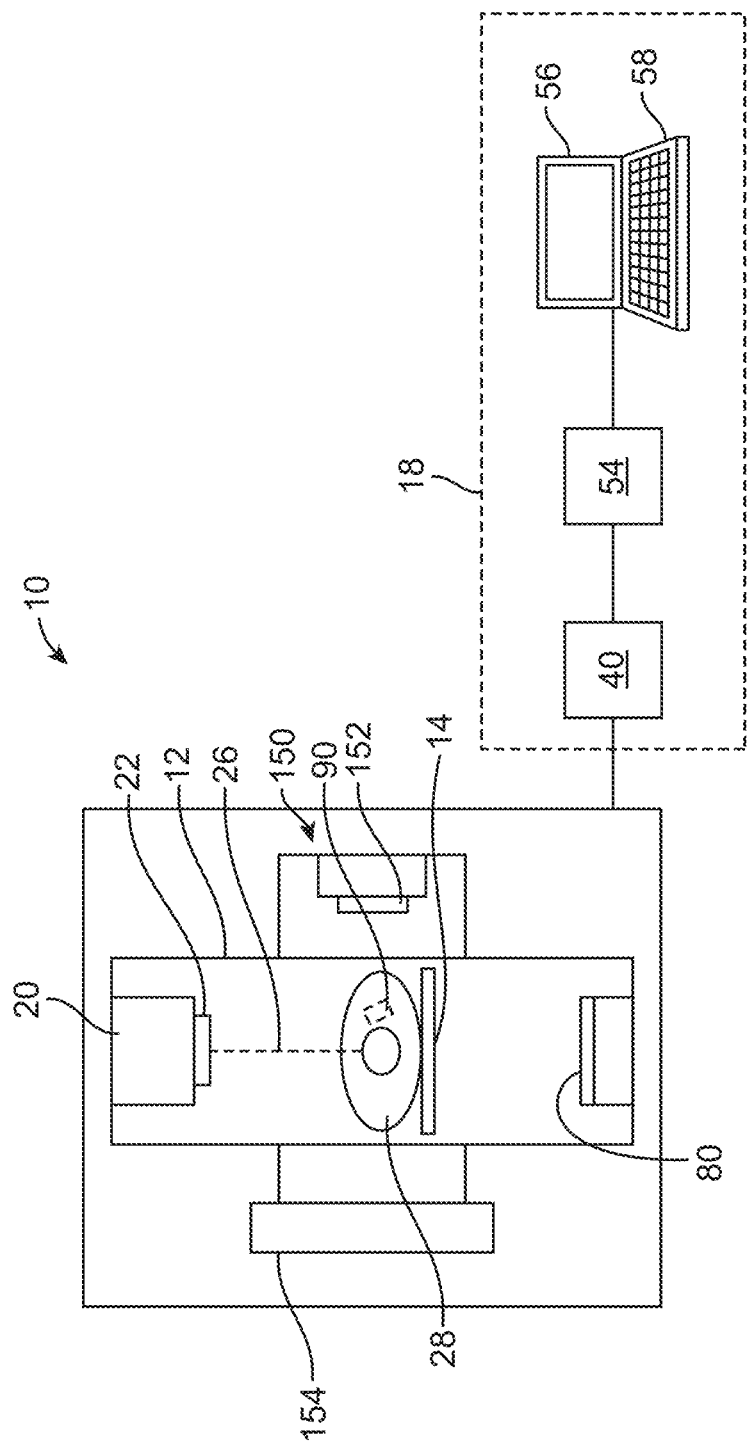
FIG. 1 illustrates a radiation system having an imaging device in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a radiation system 10. The system 10 is a treatment system that includes a gantry 12, a patient support 14 for supporting a patient 28, and a control system 18 for controlling an operation of the gantry 12. The gantry 12 is in a form of an arm, but in other embodiments, the gantry 12 may have other forms (such as a ring form, etc.). The system 10 also includes a radiation source 20 that projects a beam 26 of radiation towards a patient 28 while the patient 28 is supported on support 14, and a collimator system 22 for controlling a delivery of the radiation beam 26. The collimator 22 may be configured to adjust a cross sectional shape of the beam 26. The radiation source 20 can be configured to generate a cone beam, a fan beam, or other types of radiation beams in different embodiments.

As shown in the figure, the system 10 also includes an imager 80, located at an operative position relative to the source 20 (e.g., under the support 14). In the illustrated embodiments, the radiation source 20 is a treatment radiation source for providing treatment energy. In such cases, the treatment energy may be used to obtain images. In order to obtain imaging using treatment energies, the imager 80 is configured to generate images in response to radiation having treatment energies (e.g., MV imager). In other embodiments, in addition to being a treatment radiation source, the radiation source 20 can also be a diagnostic radiation source for providing diagnostic energy for imaging purpose. In further embodiments, the system 10 may include the radiation source 20 for providing treatment energy, and one or more other radiation sources for providing diagnostic energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. In other embodiments, the radiation source 20 may be configured to generate radiation at other energy ranges.

In the illustrated embodiments, the control system 18 includes a processing unit 54, such as a computer processor, coupled to a control 40. The control system 18 may also include a monitor 56 for displaying data and an input device 58, such as a keyboard or a mouse, for inputting data. The operation of the radiation source 20 and the gantry 12 are controlled by the control 40, which provides power and timing signals to the radiation source 20, and controls a rotational speed and position of the gantry 12, based on signals received from the processing unit 54. In some cases, the control 40 may also control the collimator system 22 and the position of the patient support 14. Although the control 40 is shown as a separate component from the gantry 12 and the processor 54, in alternative embodiments, the control 40 can be a part of the gantry 12 or the processing unit 54.

In some embodiments, the system 10 may be a treatment system configured to deliver treatment radiation beam towards the patient 28 at different gantry angles. During a treatment procedure, the source 20 rotates around the patient 28 and delivers treatment radiation beam from different gantry angles towards the patient 28. While the source 20 is at different gantry angles, the collimator 22 is operated to change the shape of the beam to correspond with a shape of the target tissue structure. For example, the collimator 22 may be operated so that the shape of the beam is similar to a cross sectional shape of the target tissue structure. In another example, the collimator 22 may be operated so that different portions of the target tissue structure receive different amount of radiation (as in an IMRT procedure).

In the illustrated embodiments, the system 10 also includes an imaging device 150 having an imaging source 150 and an imager 154. The imaging device 150 is configured to obtain one or more images of an internal part of the patient 28. The image(s) obtained by the imaging device 150 may be used to monitor a position of the patient 28. In some cases, the imaging device 150 may be configured to obtain images of an internal fiducial 90 of the patient 28. The internal fiducial 90 may be an internal structure inside the patient 28. In some embodiments, the internal structure may move in correspondence (e.g., in sync) with a target of the patient 28 that is desired to be treated. In such cases, the internal structure may be used as a surrogate for determining a position and/or movement of the target during treatment of the patient 28, and motion management based on the surrogate may be employed in some cases. Thus, the internal fiducial 90 may be imaged by the imaging device 150 (or radiation source 20 and imager 80) that functions as a position monitoring system during a treatment of the patient 28. By means of non-limiting examples, the internal fiducial 90 may be an anatomical surrogate, such as bony structure, a vessel, a natural calcification, or any other items in a body.

In some embodiments, the imaging device 150 may be an x-ray device. In such cases, the imaging source 150 comprises a radiation source. In other embodiments, the imaging device 150 may have other configurations, and may be configured to generate images using other imaging techniques. For example, in other embodiments, the imaging device 150 may be an ultrasound imaging device, a MRI device, a tomosynthesis imaging device, or any of other types of imaging devices. Also, in the above embodiments, the imaging device 150 is illustrated as being integrated with the treatment machine. In other embodiments, the imaging device 150 may be a separate device that is separate from the treatment machine. In addition, in some embodiments, the imaging device 150 may be a room-based imaging system or a couch based imaging system. In either case, the imaging device 150 may provide any form of imaging, such as x-ray imaging, ultrasound imaging, MRI, etc. Furthermore, in other embodiments, the imaging device 150 may provide in-line imaging in the sense that it may be configured to acquire images along the same direction as the treatment beam. For example, a dual-energy source may be provided to provide imaging energy for generating an image, and to provide treatment energy to treat a patient along the same direction. In still further embodiments, the imaging device 150 may be configured to provide dual energy imaging and any form of energy-resolved imaging to increase contrast in x-ray images. For example, a first part of an image may be generated using a first energy, and a second part (e.g., a more relevant part that includes a target) of the same image may be generated using a second energy that is higher than the first energy. As a result, the second part of the image will have higher contrast compared to the first part. However, the overall dose involved in generating the whole image may be reduced compared to the situation in which the entire image is generated using the second energy.

Before the system 10 is used to treat the patient 28, a treatment plan is first determined for the patient 28. For example, a technician may obtain a treatment plan image of the patient 28, and may process the treatment plan image to create the treatment plan. By means of non-limiting examples, the treatment plan image may be a CT image, a PET-CT image, a SPECT-CT image, an x-ray image, an ultrasound image, a MRI image, a tomosynthesis image, etc. When creating the treatment plan, a treatment plan software (application) may be utilized to assist the user to create the treatment plan by optimizing treatment parameters. For example, the user may use the treatment plan software to delineate anatomical structures (target and critical organs) in the patient 28, and determine different beam delivery angles for delivering treatment energies towards the target while minimizing delivery of the energies to the critical organs. The user may also use the treatment plan software to create constraints (e.g., minimum dose to be delivered to the target, maximum allowable dose for critical organs, etc.) for the treatment planning. The treatment plan may be stored as an electronic file, and may be retrieved by the system 10 at a later time.

To perform treatment, the system 10 retrieves the stored treatment plan (e.g., from a medium), and processes the treatment plan to deliver treatment energies towards the target in the patient 28. For example, a processor of the system 10 may electronically process the treatment plan to activate one or more components of the system 10 to deliver the treatment energy. The processor of the system 10 may cause the gantry 12 to rotate to a certain gantry angle prescribed by the treatment plan, and to deliver certain amount of treatment energy from the gantry angle towards the target in the patient 28. The processor of the system 10 may also control the collimator 22 to shape the beam 26 while the energy source 20 is at the gantry angle. The treatment plan may prescribe that treatment energies be delivered from multiple gantry angles. Also, the treatment plan may prescribe that the patient be treated multiple times on multiple days.

Radiation treatment may include multiple fractions, and it is desirable that radiation be delivered to the target in all of the fractions. In some cases at the time of treatment, treatment parameters required to deliver radiation to the target might differ considerably from the treatment parameters used in the original treatment plan, due to, for example, internal organ movement (e.g., bladder filling, bowel movement, etc.), patient weight loss, tumor shrinkage, etc. In certain occasions, if the difference between the treatment parameters at the time of treatment and the treatment parameters used in the original treatment plan is too great, the goal of the treatment may no longer be met. In such cases, a new treatment plan is needed. Based on knowledge and assessment of the treatment parameter differences, the user decides if the patient needs a new treatment plan or if the original treatment plan is sufficient. If a re-plan is needed, the user may then use the treatment planning software to perform a re-planning to determine a new treatment plan.

Figure 2:
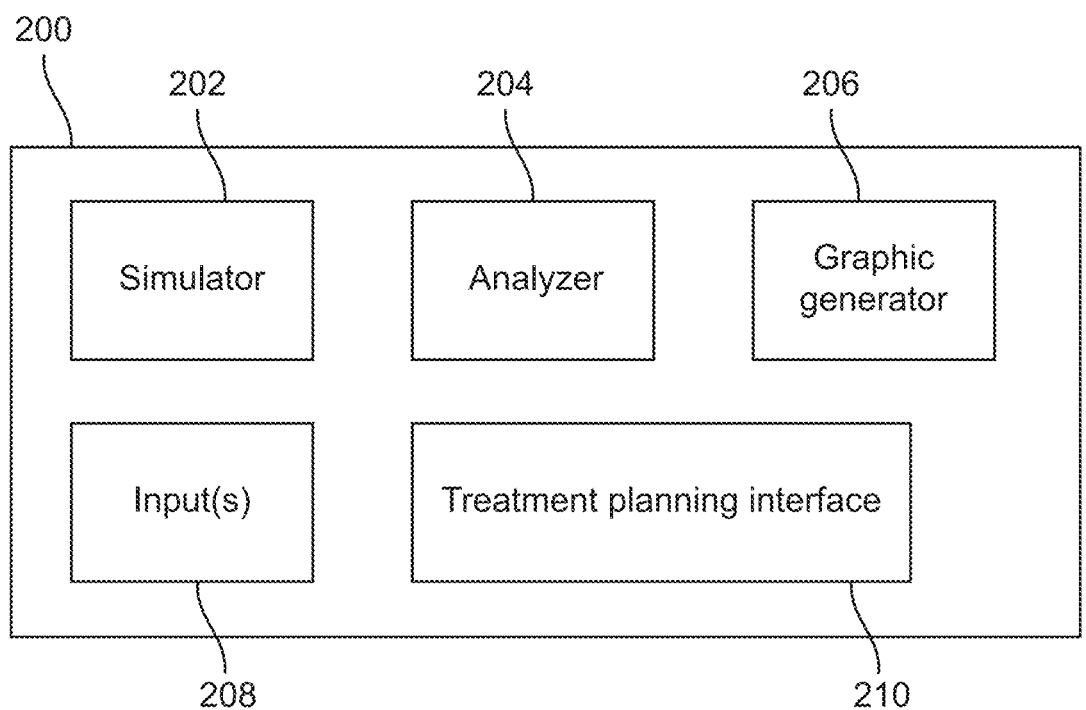
FIG. 2 illustrates an apparatus for treatment planning in accordance with some embodiments.

FIG. 2 illustrates an apparatus 200 for treatment planning in accordance with some embodiments. The apparatus 200 includes a simulator 202 configured to obtain a first model representing a first component of a medical system, and virtually move the first model to simulate a movement of the first component of the medical system. The apparatus 200 also includes an analyzer 204 configured to determine imaging waypoints at which imaging is possible during a treatment process based on the virtual movement of the first model. The apparatus 200 further includes a graphic generator 210 configured to generate a graphic based on the determined imaging waypoints.

In some embodiments, the simulator 202 may be configured to also obtain a second model representing the patient support 14, and virtually move the second model to simulate a movement of the patient support 14. Also, in some embodiments, the simulator 202 may be configured to obtain a surface model of a patient 28, and virtually move the surface model to simulate a movement of the patient 28 due to a movement of a patient support 14. The surface model of the patient 28 may be obtained using a surface scanner. The surface model may be a "patient and couch outline" that also include a part of the patient support 14. In some cases, the surface scanner may be implemented at a CT machine. In the case where the "patient and couch outline" is not available for planning (e.g., if there is no surface scanner), then a user interface may be provided to a user to allow the user to select default patient surfaces of variable sizes for the planning process. In some cases, the input for the size selection may be a CT scan performed by the CT machine.

Furthermore, in some cases, the user interface may allow the user to input one or more parameters (e.g., imaging geometry (such as source-to-imager distance, imaging distance, etc.), amount of imaging, machine geometry, etc.) for determining the waypoints.

In some embodiments, when the simulator 202 virtually moves the first model and/or the second model, the simulator 202 considers degrees of freedom for the respective objects represented by the first and second models. For example, if the component represented by the first model is the source 20 which is configured to turn about an axis, then the simulator 202 is configured to consider its circular movement when virtually moving the first model. As another example, if the component represented by the first model is an imaging panel that translates along a certain path, then the simulator 202 is configured to consider the path of the imaging panel when virtually moving the first model.

The analyzer 204 is configured to determine one or more imaging waypoints representing the stage(s) of the planned treatment where imaging is possible. In some embodiments, the analyzer 204 may be configured to obtain geometry (size, shape, etc.) of different objects represented by the different models, and to determine a set of system configurations in which imaging (based on user defined parameters) is possible based on the geometry of the different objects, and virtual movements of the objects. In some embodiments, the simulator 202 and/or the analyzer 204 may be a part of a collision analyzer configured to determine a set of system configurations which do not result in components' collision, and identify imaging waypoints that correspond with those system configurations. For example, assume that at a certain system configuration, the imager is at position (X, Y, Z), the patient support is at position (A, B, C), and the imager and the patient support do not collide at such positions. The analyzer 204 may determine that imaging is possible in such system configuration. Assuming such system configuration occurs at a certain control point index (which represents a progress of a treatment to be executed), the analyzer 204 may then assign such control point index as an imaging waypoint for the type of imaging provided by the imager being considered. By identifying a set of control point indices at which imaging is possible, the analyzer 204 may then determine a set of imaging waypoints for the particular type of imaging.

In addition, the determination of the imaging waypoints by the analyzer 204 may consider user inputs. For example, if the user selects kV imaging as a desired imaging option, and also inputs a value X as an imaging distance, the analyzer 204 may then determine imaging waypoints based on the selected type of imaging, and also based on the prescribed imaging distance X. In the illustrated example, the user input "imaging distance X" will cause the simulator 202 to adjust a spatial relationship between the model of the patient support and the model of the imager, so that the spacing between the two models corresponds with the imaging distance X. The virtual movements of the models by the simulator 202, and the determination of the imaging waypoints by the analyzer 204, will then be based at least in part on the modeling of the system that includes the imaging distance X. In some embodiments, the apparatus 200 may provide a user interface that allows a user to input different parameters to define the system being modeled. For example, in addition to imaging distance, the user interface may also allow a user to define source to imager distance, length of imager arm, degrees of freedom for the various system components, etc. The apparatus 200 may then utilize such user inputs to create a model of the system that includes the various components.

As shown in FIG. 2, the apparatus 200 may further include one or more input(s) 208 for receiving input from a user. For example, the input may be a user-defined amount of imaging coverage. In such cases, the analyzer 204 is configured to determine the imaging waypoints based on the user-defined amount of imaging coverage. Alternatively, or additionally, the input may include imaging source type (e.g., MV imaging source, kV imaging source, hybrid sources, etc.). In such cases, the analyzer 204 is configured to determine the imaging waypoints based on the user-prescribed imaging source type(s). The input may also include a user-prescribed type of imaging (e.g., continuous imaging, triggered imaging, single paired imaging, etc.). In such cases, the analyzer 204 is configured to determine the imaging waypoints based on the user-prescribed type(s) of imaging. Furthermore, the input may include a user-prescribed verification scheme.

Figure 3:
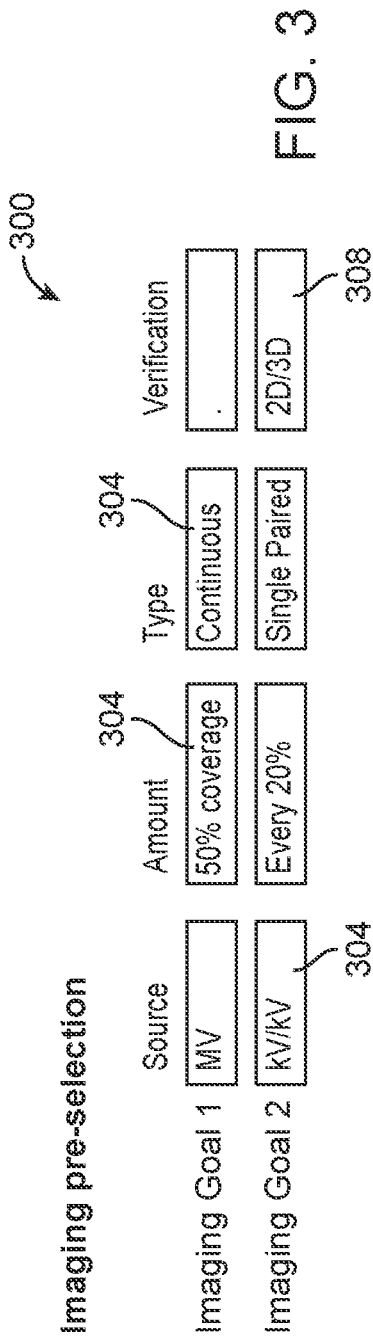
FIG. 3 illustrates a user interface in accordance with some embodiments.

FIG. 3 illustrates a user interface 300 that is configured to allow a user to input one or more parameters, based on which the analyzer 204 is configured to generate imaging waypoints. As shown in the figure, the user interface 300 includes a field 302 for allowing a user to provide a user-defined amount of imaging coverage, a field 304 for allowing the user to select or identify imaging source type, a field 306 for allowing the user to select or identify a type of imaging, and a filed 308 for allowing the user to indicate a desired verification scheme.

Turning back to FIG. 2, in some embodiments, the apparatus 200 may be a part of a treatment planning system. In other embodiments, the apparatus 200 may be a separate module that operates and communicates with a treatment planning system. In further embodiments, the apparatus 200 may be a part of a treatment system, or may be a separate module that operates and communicates with the treatment system.

In some embodiments, the imaging waypoints determined by the analyzer 204 comprise a first set of imaging waypoints and a second set of imaging waypoints, and wherein the analyzer 204 is configured to determine the first set of imaging waypoints for a first type of imaging, and to determine the second set of imaging waypoints for a second type of imaging. As an example, the first type of imaging comprises kV-imaging, and the second type of imaging comprises MV-imaging. As another example, the first type of imaging may be imaging based on a first imaging distance, and the second type of imaging may be imaging based on a second imaging distance. As a further example, the first type of imaging may be a first angle offset between two imager (e.g., kV-imager) positions, and the second type of imaging may be a second angle offset between two imager positions.

In some embodiments, the graphic generator 206 is configured to generate a graphic to present the imaging waypoints as control point indices (FIG. 4A). By means of non-limiting examples, the control point indices may comprise or may represent: gantry angles, couch angles, time points, doses, etc. As shown in FIG. 4A, two sets 400, 402 of imaging waypoints are presented graphically for two respective types 410, 412 of imaging. In other examples, there may be more than two types of imaging, or just a single type of imaging. Also, in the example, the two types of imaging are MV imaging and kV imaging. In other examples, the types of imaging for which the imaging waypoints are presented may be different from MV and kV.

In some embodiments, the type of imaging for which the imaging waypoints are presented may be hybrid imaging (i.e., imaging that involves multi-energy, such as kV+MV).

In some cases, after the imaging waypoints have been presented to the user in a user interface, the user interface may allow the user to select one or more imaging waypoints to prescribe imaging that is desired to be performed during treatment. The selected imaging waypoint(s) may be stored as a part of a treatment plan.

Figure 4B:
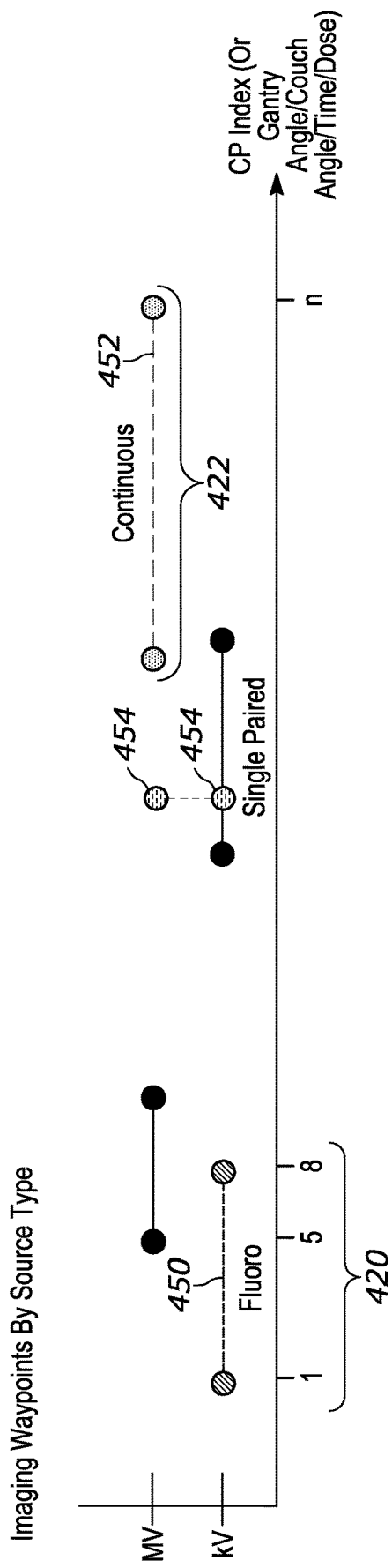

FIG. 4B illustrates a selection 450 of a subset 420 of the imaging waypoints in the first set 400 for performing fluoroscopic imaging, a selection 452 of a subset 422 of the imaging waypoints in the second set 402 for performing continuous imaging, and a selection 454 of a pair of imaging waypoints (a first imaging waypoint from the first set 400, and a second imaging waypoint from the second set 402) for performing a single pair of imaging.

Figure 5A:
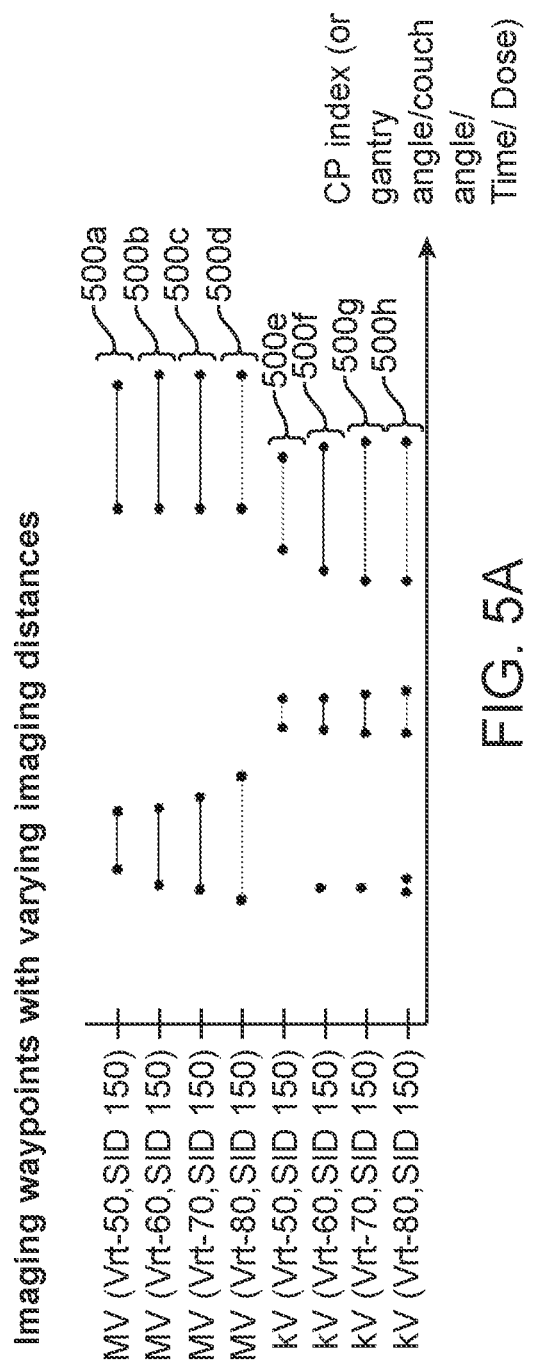
FIGS. 5A-5B illustrate imaging waypoints by source type and varying imager distances.

In other embodiments, the imaging waypoints may be arranged in the graphic as a function of imaging distance (FIG. 5A). An imaging distance (Vrt) may be varied by moving the patient support 14 (FIG. 1) relative to the imager 80/154, moving the imager 80/154 relative to the patient support 14, or moving both the imager 80/154 and the patient support 14, to thereby change a distance between the patient 80 and the imager 80/154. As shown in FIG. 5A, four sets 500a-500d of imaging waypoints are presented graphically for MV imaging with four different imaging distances, respectively, and four sets 500e-500h of imaging waypoints are presented graphically for kV imaging with four different imaging distances, respectively. In other embodiments, the number of imaging distances being presented graphically may be more than four, or fewer than four. Also, in other embodiments, instead of two types of imaging, the imaging waypoints may be presented graphically for more than two types of imaging, or fewer than two types (i.e., one type only) of imaging.

Figure 5B:
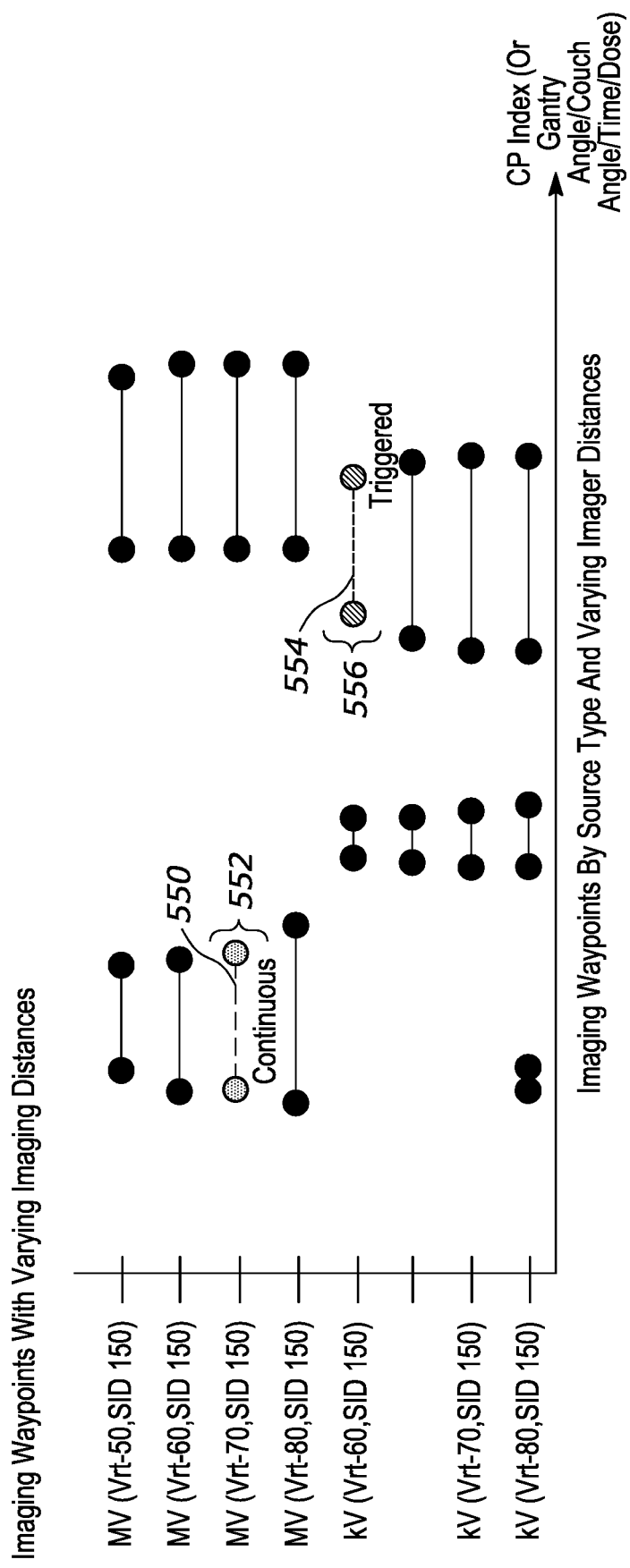

FIG. 5B illustrates a selection 550 of a subset 552 of the imaging waypoints in the set 500c for performing continuous imaging, and a selection 554 of a subset 556 of the imaging waypoints in the set 500e for performing triggered imaging.

Figure 6A:
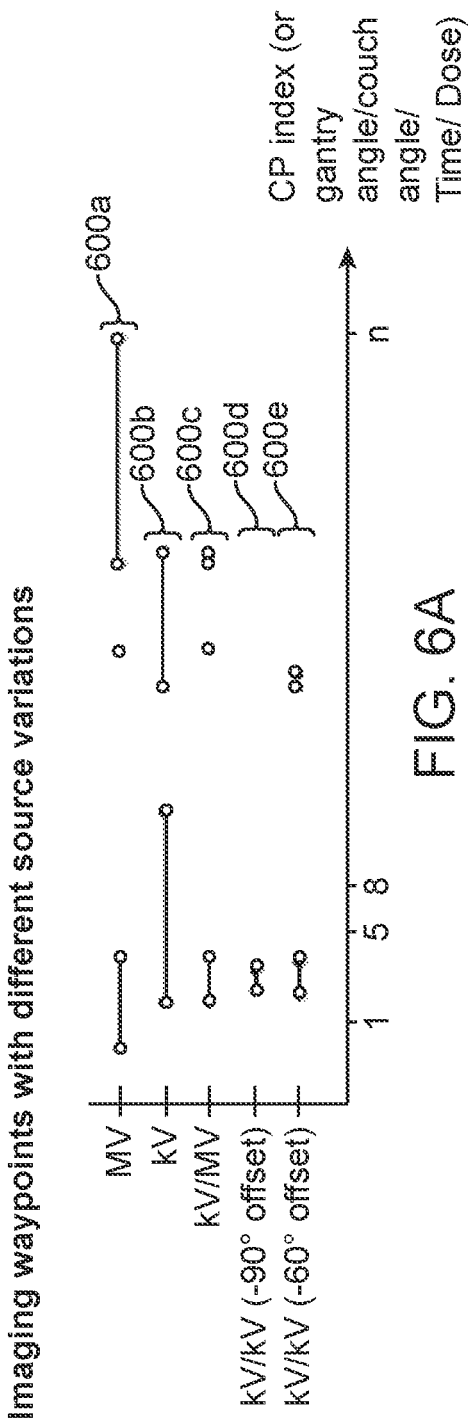
FIGS. 6A-6B illustrate imaging waypoints with different source combinations.

In some embodiments, the imaging waypoints are arranged in a graphic as a function of angle offset between two kV-imager positions. For example, as shown in FIG. 6A, in addition to the types of imaging, the imaging waypoints may be arranged in a graphic as a function of angle offset between two kV-imager positions. As shown in FIG. 6A, a first set 600a of imaging waypoints is presented graphically for MV imaging, a second set 600b of imaging waypoints is presented graphically for kV imaging, a third set 600c of imaging waypoints is presented graphically for kV/MV imaging, a fourth set 600d of imaging waypoints is presented graphically for kV/kV imaging in which the kV-imager positions are separated by 90°, and a fifth set 600e of imaging waypoints is presented graphically for kV/kV imaging in which the kV-imager positions are separated by 60°. In other embodiments, the number of imaging offsets being presented graphically may be more than two, or fewer than two. As shown in the figure, the kV/MV imaging waypoints in the third set 600c are obtained by filtering imaging waypoints that are common to both the first set 600a and the second set 600b.

Figure 6B:
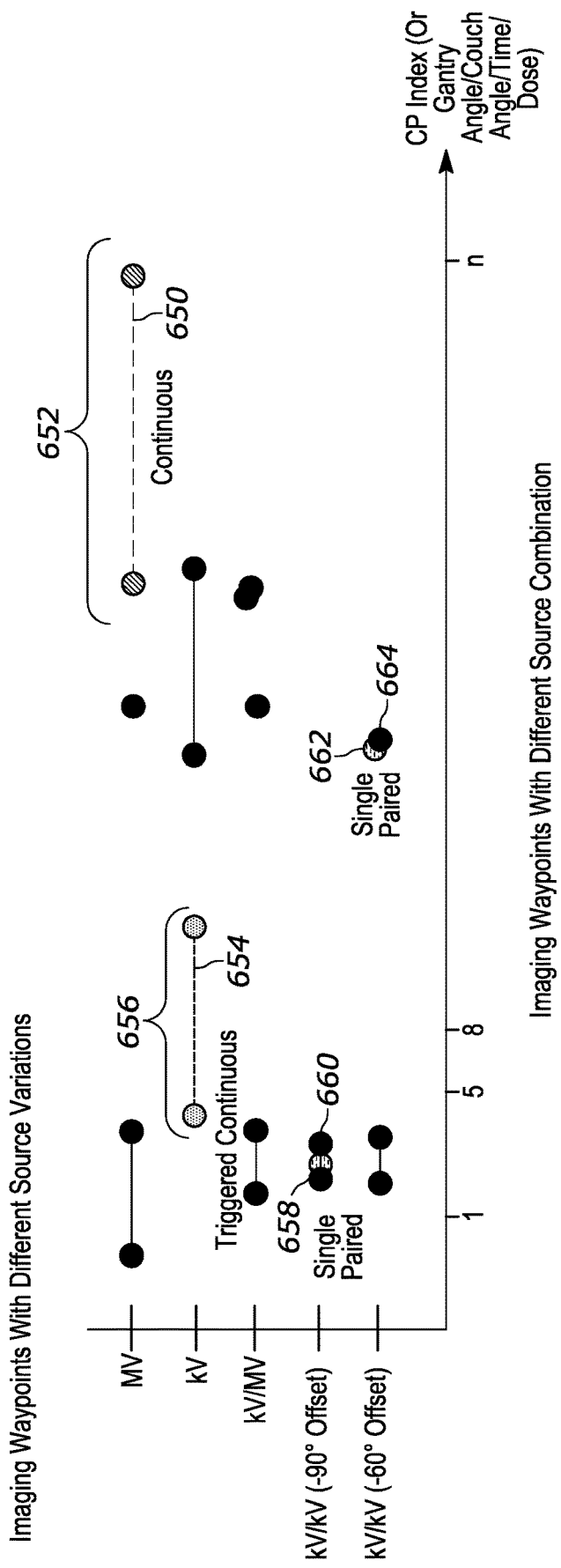

FIG. 6B illustrates a selection 650 of a subset 652 of the imaging waypoints in the first set 600a for performing continuous imaging, a selection 654 of a subset 656 of the imaging waypoints in the second set 600b for performing triggered imaging, a selection 658 of a subset 660 of imaging waypoints in the fourth set 600d for performing kV/kV imaging in which the imaging positions are separated by 90°, and a selection 662 of a subset 664 of imaging waypoints in the fifth set 600e for performing kV/kV imaging in which the imaging positions are separated by 60°.

Figure 7:
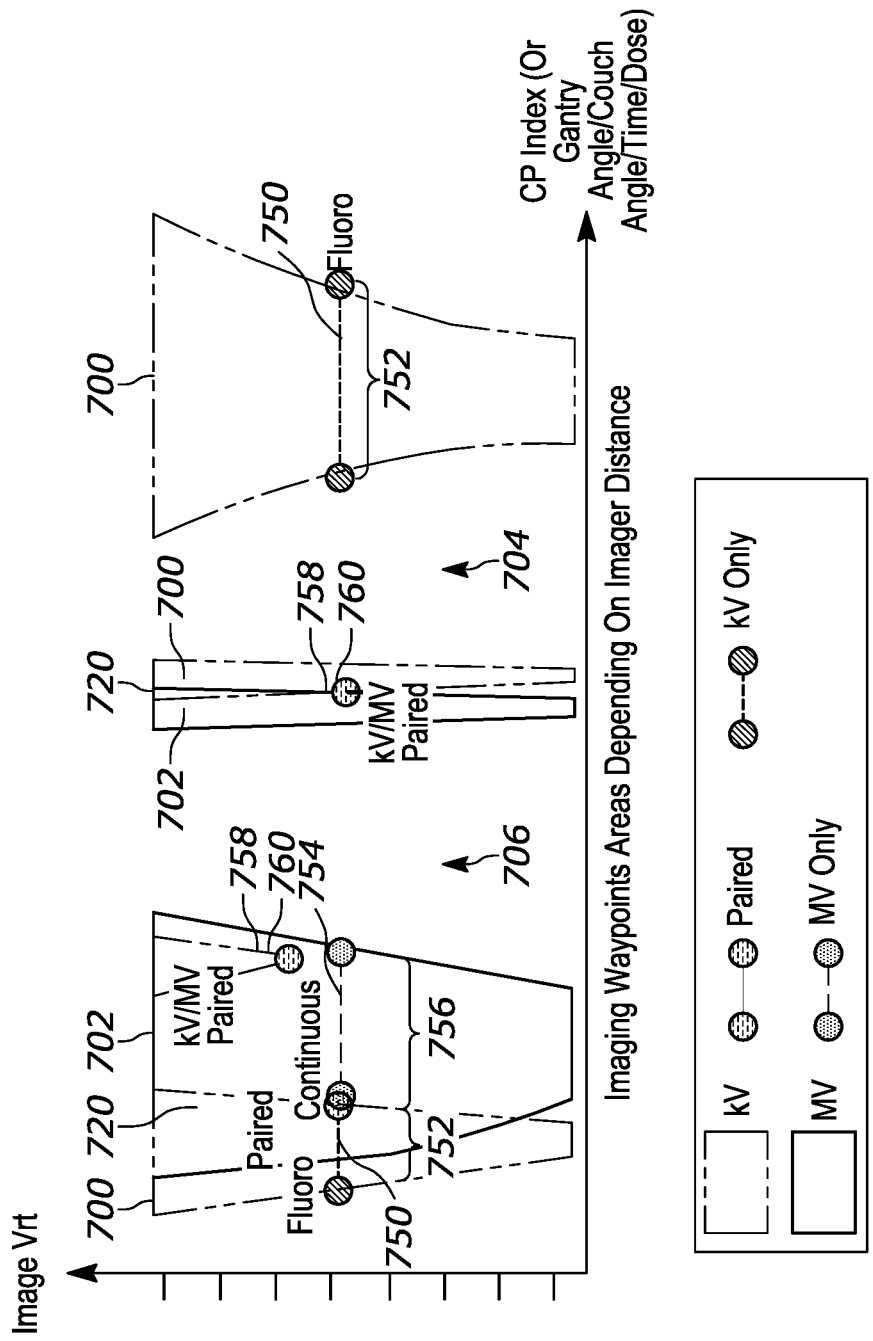
FIG. 7 illustrates imaging waypoints areas with varying imager distance.

In the above embodiments, different sets of imaging waypoints for different imaging distances are presented graphically as a function of control point index. In other embodiments, instead of presenting the different sets of imaging waypoints for different imaging distances individually, the imaging distance may be presented graphically in a continuous manner. For example, as shown in FIG. 7, values of the imaging distance are presented in a continuous manner, and values of the imaging waypoints are also presented in a continuous manner. Accordingly, the imaging distance and the imaging waypoints define one or more two-dimensional areas in the graphic. Also, as shown in the graphic of FIG. 7, the imaging waypoints are arranged into two groups, wherein a first group 700 of the imaging waypoints is for a first type of imaging (e.g., kV imaging), and a second group 702 of the imaging waypoints is for a second type of imaging (e.g., MV imaging). In the first group 700 of the imaging waypoints, there are multiple areas in the graphic that are spaced apart from each other. For example, spacing 704 depicts the case where for a certain control point index, there are no imaging waypoints available for any of the imaging distance for kV imaging. Similarly, in the second group 702 of the imaging waypoints, there are multiple areas in the graphic that are spaced apart from each other. The spacing 706 depicts the case where for a certain control point index, there are no imaging waypoints available for any of the imaging distance for MV imaging.

As shown in FIG. 7, the first group 700 of the imaging waypoints and the second group 702 of the imaging waypoints have certain overlapping area(s) 720. The overlapping area(s) 720 indicate imaging waypoints that are available for both types of imaging (e.g., kV and MV imaging). In addition, as shown in FIG. 7, a user may make a selection 750 of a subset 752 of the imaging waypoints for performing kV imaging, may make a selection 754 of a subset 756 of the imaging waypoints for performing MV imaging, and/or may make a selection 758 of a subset 760 of the imaging waypoints for performing both kV and MV imaging.

In the above embodiments, two types of imaging are shown in the graphic. In other embodiments, the graphic may show imaging waypoints for more than two types of imaging, or may show imaging waypoints for only one type of imaging. Also, in other embodiments, the types of imaging may be different from kV imaging and MV imaging, and may be other types of imaging.

Figure 8:
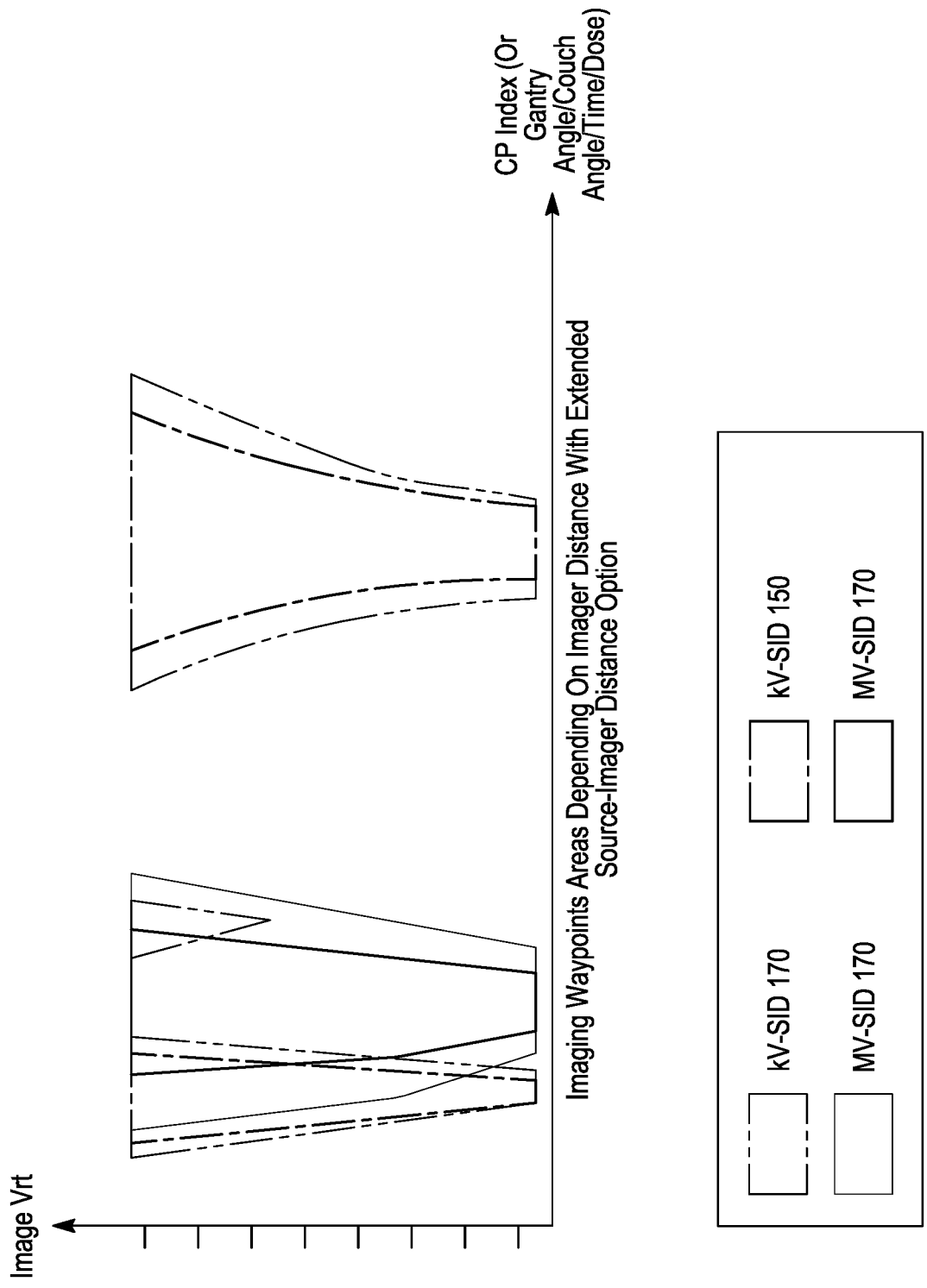
FIG. 8 illustrates imaging waypoints areas with varying imager distance and extended source-to-imager distance option.

In some embodiments, the type of imaging may further be sub-divided based on source-to-imaging distance (SID). SID may be varied by moving the source 20 (shown in FIG. 1) relative to the imager 80/154 (e.g., increasing or decreasing the distance therebetween), moving the imager 80/154 relative to the source 20, or moving both the imager 80/154 and the source 20. FIG. 8 illustrates a graphic that is similar to that shown in FIG. 7, except that the imaging waypoints are presented not only with respect to the different types of imaging, but also with respect to different SIDs. As shown in the figure, four groups of imaging waypoints are shown, which include kV imaging with SID of 170, kV imaging with SID of 150, MV imaging with SID of 170, and MV imaging with SID of 150. The four groups of imaging waypoints may be represented in the graphic as different respective colors in the graphic. In other embodiments, the four groups of imaging waypoints may be represented as different areas with different shadings, fillings, hatched patterns, etc. Furthermore, in other embodiments, there may be more than four groups of imaging waypoints, or fewer than four groups of imaging waypoints. For example, there may be other groups of imaging waypoints for other SIDs that are different from "170" and "150". Although not shown in the figure, in some embodiments, a user may make one or more selection(s) on the graphic for performing different imaging (e.g., kV imaging, MV imaging, kV-MV imaging, triggered imaging, continuous imaging, etc.), like that shown in FIG. 7.

Figure 9:
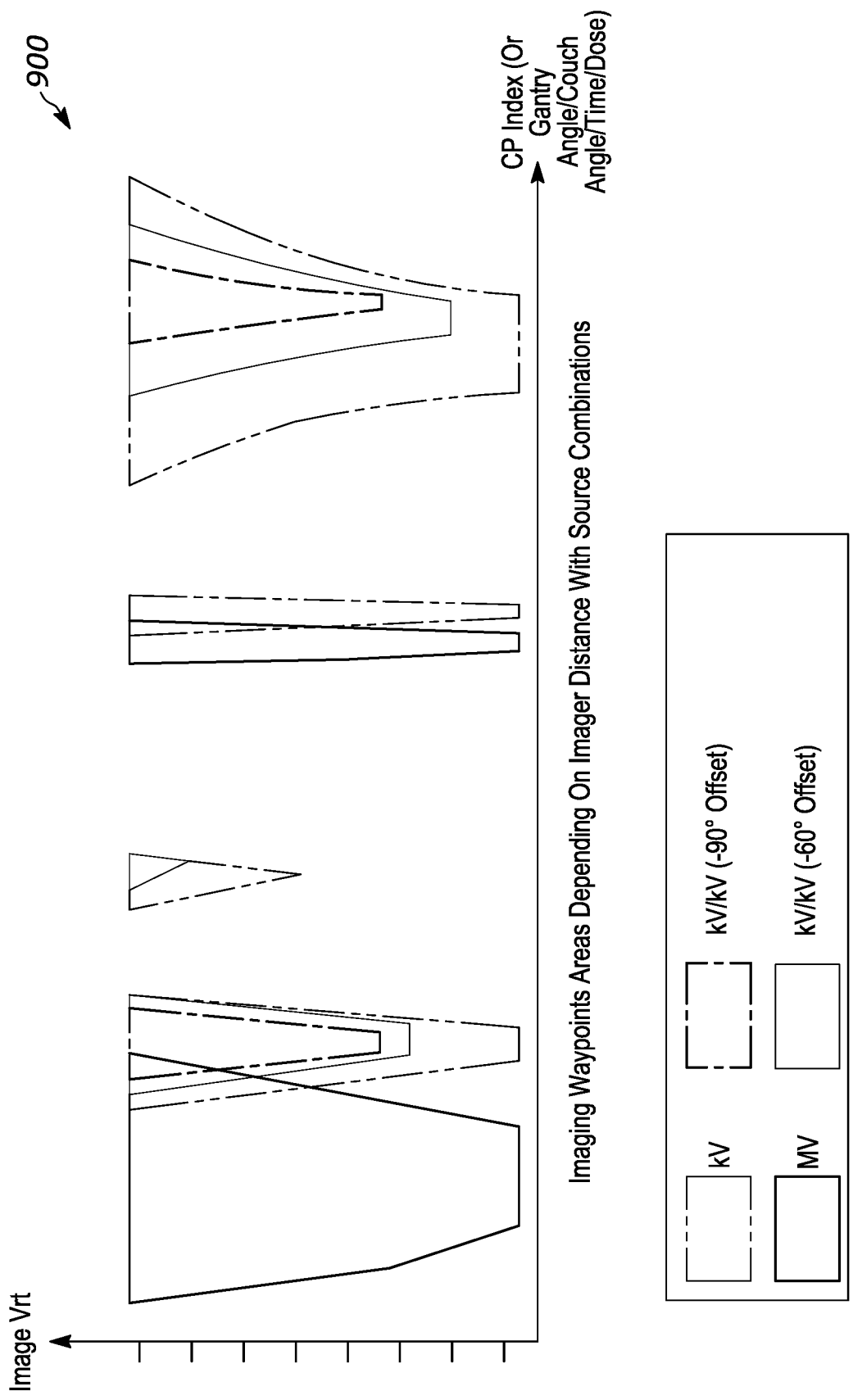
FIG. 9 illustrates imaging waypoints areas with varying imager distance and source combinations.

In some embodiments, the type of imaging may further be sub-divided based on offsets of imager positions. FIG. 9 illustrates a graphic 900 that is similar to that shown in FIG. 7, except that the imaging waypoints are presented not only with respect to the different types of imaging, but also with respect to different offsets of imager positions. As shown in FIG. 9, four groups of imaging waypoints are shown, which include kV imaging, kV imaging with offset of imager positions being 90°, MV imaging, and kV imaging with offset of imager positions being 60°. The area for kV imaging with offset (90°/60°) of imager positions is located in the area for kV imaging because the imaging waypoints for such imaging (kV/kV imaging with imager positions offset) are a subset of the imaging waypoints for kV imaging. The four groups of imaging waypoints may be represented as different respective colors in the graphic. In other embodiments, the four groups of imaging waypoints may be represented as different areas with different shadings, fillings, hatched patterns, etc. Furthermore, in other embodiments, there may be more than four groups of imaging waypoints, or fewer than four groups of imaging waypoints. For example, there may be other groups of imaging waypoints for other offsets of imager positions that are different from 90° and 60°. Although not shown in the figure, in some embodiments, a user may make one or more selection(s) on the graphic for performing different imaging (e.g., kV imaging, MV imaging, kV-MV imaging, triggered imaging, continuous imaging, etc.), like that shown in FIG. 7.

Figure 10:
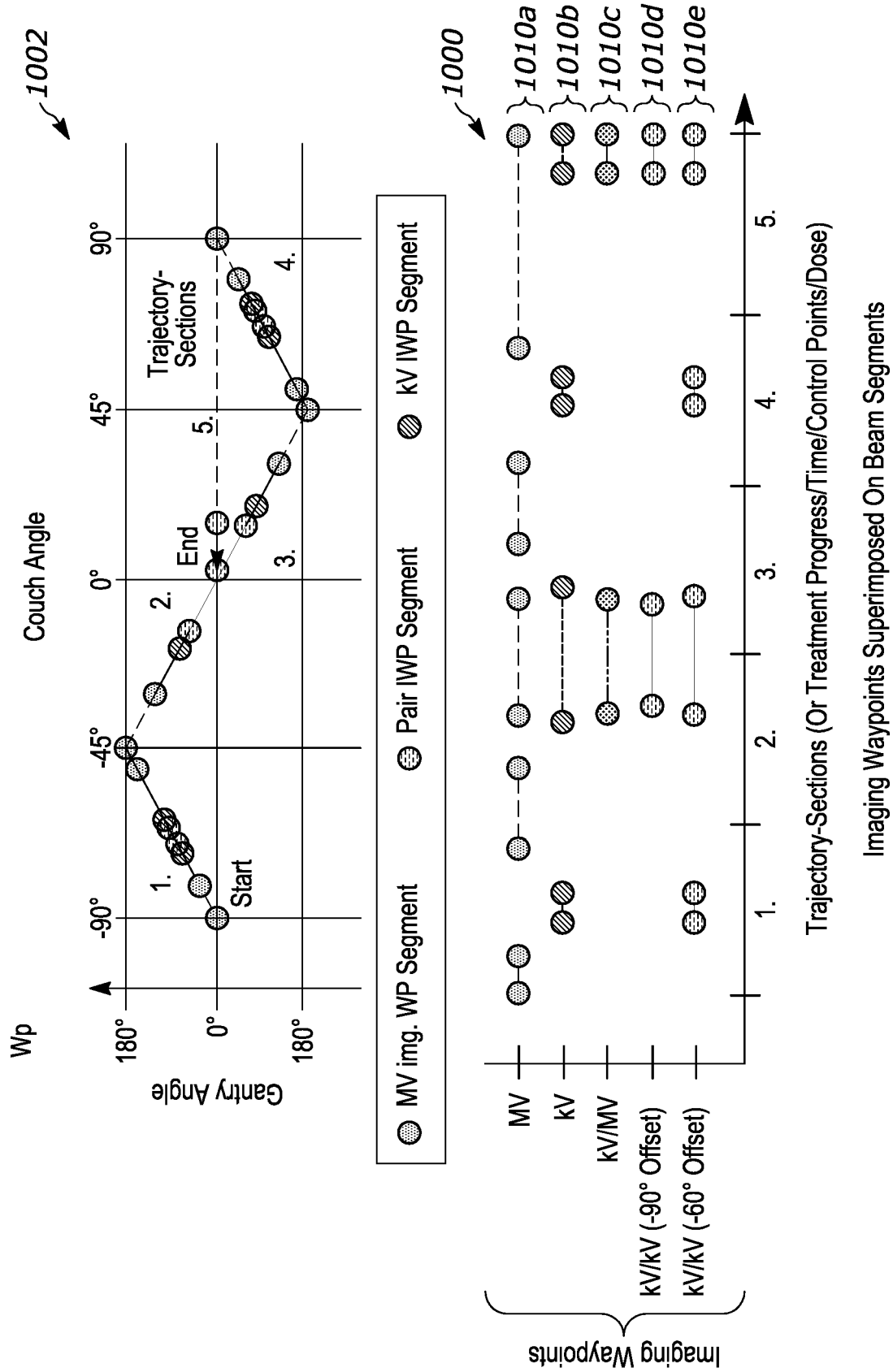
FIG. 10 illustrates imaging waypoints superimposed on beam segments.

In some embodiments, in addition to providing the graphic for presenting the imaging waypoints, the graphic generator 206, shown in FIG. 2, may be configured to also provide a diagram indicating how a couch angle varies in relation to a gantry angle. FIG. 10 illustrates a graphic having a first diagram 1000 that presents different sets of imaging waypoints. The graphic further includes a second diagram 1002 that corresponds with the first diagram 1000.

The first diagram 1000 is similar to that shown in FIG. 6A. As shown in FIG. 10, a first set 1010a of imaging waypoints is presented graphically for MV imaging, a second set 1010b of imaging waypoints is presented graphically for kV imaging, a third set 1010c of imaging waypoints is presented graphically for kV/MV imaging, a fourth set 1010d of imaging waypoints is presented graphically for kV/kV imaging in which the kV-imager positions are separated by 90°, and a fifth set 1010e of imaging waypoints is presented graphically for kV/kV imaging in which the kV-imager positions are separated by 60°. In other embodiments, the number of imaging offsets being presented graphically may be more than two, or fewer than two. As shown in FIG. 10, the kV/MV imaging waypoints in the third set 1010c are obtained by filtering imaging waypoints that are common to both the first set 1010a and the second set 1010b. The imaging waypoints in diagram 1000 are also presented in diagram 1002.

As shown in diagram 1002, when the gantry is at 0°, the couch angle is at −90°. As the gantry is rotated from 0° to 180°, the couch is also rotated from −90° to −45° (as represented by trajectory section 1). Then as the gantry rotates from 180° to 0°, the couch is rotated from −45° to 0° (as represented by trajectory section 2). Next, as the gantry rotates from 0° to −180°, the couch is rotated from 0° to 45° (as represented by trajectory section 3). Next, as the gantry rotates from −180° to 0°, the couch rotates from 45° to 90° (as represented by trajectory section 4). Next, the gantry stays at 0°, and the couch is rotated from 90° to 0° (as represented by trajectory section 5). Thus, the diagram 1002 is advantageous in that it allows a spatial relationship between the gantry and the patient support during different trajectories to be presented graphically.

As shown in the diagram 1002, the imaging waypoints for the various sets in the diagram 1000 are superimposed on beam segments/trajectories in the diagram 1002. Since the x-axis of the diagram 1000 represents control point indices that correspond with a progression of a treatment process, the x-axis can be divided into different segments to form different trajectories. Different color codes and/or graphics may be used to represent the imaging waypoints in the different respective sets. As shown in the diagrams 1000, 1002, the x-axis of the diagram 1000 is divided into five segments, which are presented as five respective beam segments/trajectories in the diagram 1002. This way, a user can see what type of imaging is possible, and where such imaging is possible, at each of the different trajectories. As shown in the example, in some cases, different types of imaging may be possible in a beam segment/trajectory. In other cases, only one type of imaging, or no imaging, is possible for a certain beam segment/trajectory.

Figure 11:
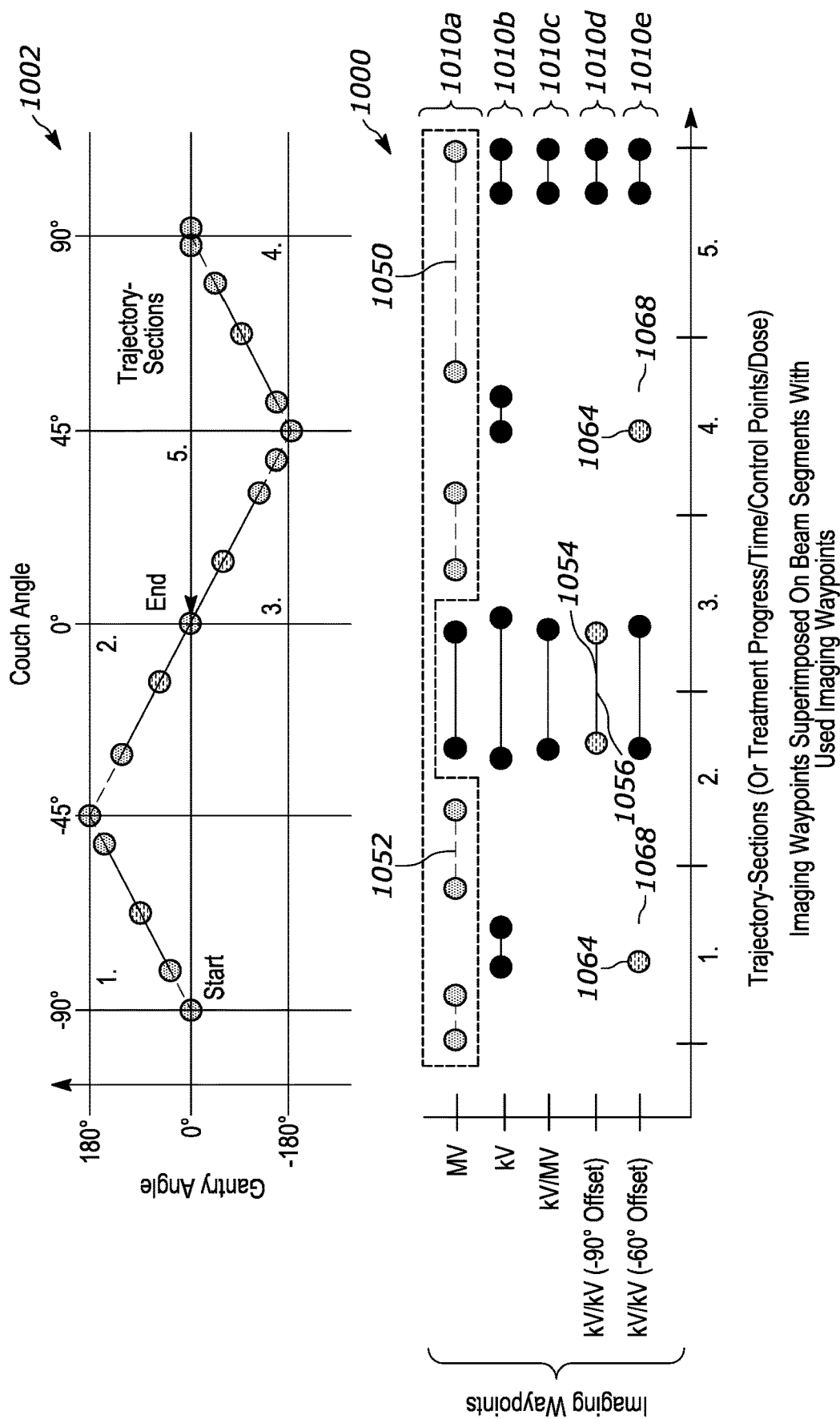
FIG. 11 illustrates imaging waypoints superimposed on beam segments with used imaging waypoints.

FIG. 11 illustrates a selection 1050 of a subset 1052 of the imaging waypoints in the first set 1010a, a selection 1054 of a subset 1056 of the imaging waypoints in the fourth set 1010d, and a selection 1064 of a subset 1068 of imaging waypoints in the fifth set 600e, for use in a treatment plan. The selected imaging waypoints are shown also in the diagram 1002. Different color codes and/or graphics may be used to represent the selected imaging waypoints in the different respective sets.

In some embodiments, as shown in FIG. 2, the analyzer 204 may be configured to determine gantry angle of a gantry associated with a treatment energy source as a function of control point index. In such cases, the graphic generator 206 may be configured to provide a diagram indicating the gantry angle as the function of the control point index. An example of a diagram 1200 is illustrated in FIG. 12.

Also, in some embodiments, analyzer 204 shown in FIG. 2 may be configured to determine couch angle of a couch as a function of control point index. In such cases, the graphic generator 206 may be configured to provide a diagram indicating the couch angle as a function of the control point index. An example of a diagram 1202 is illustrated in FIG. 12.

Figure 12:
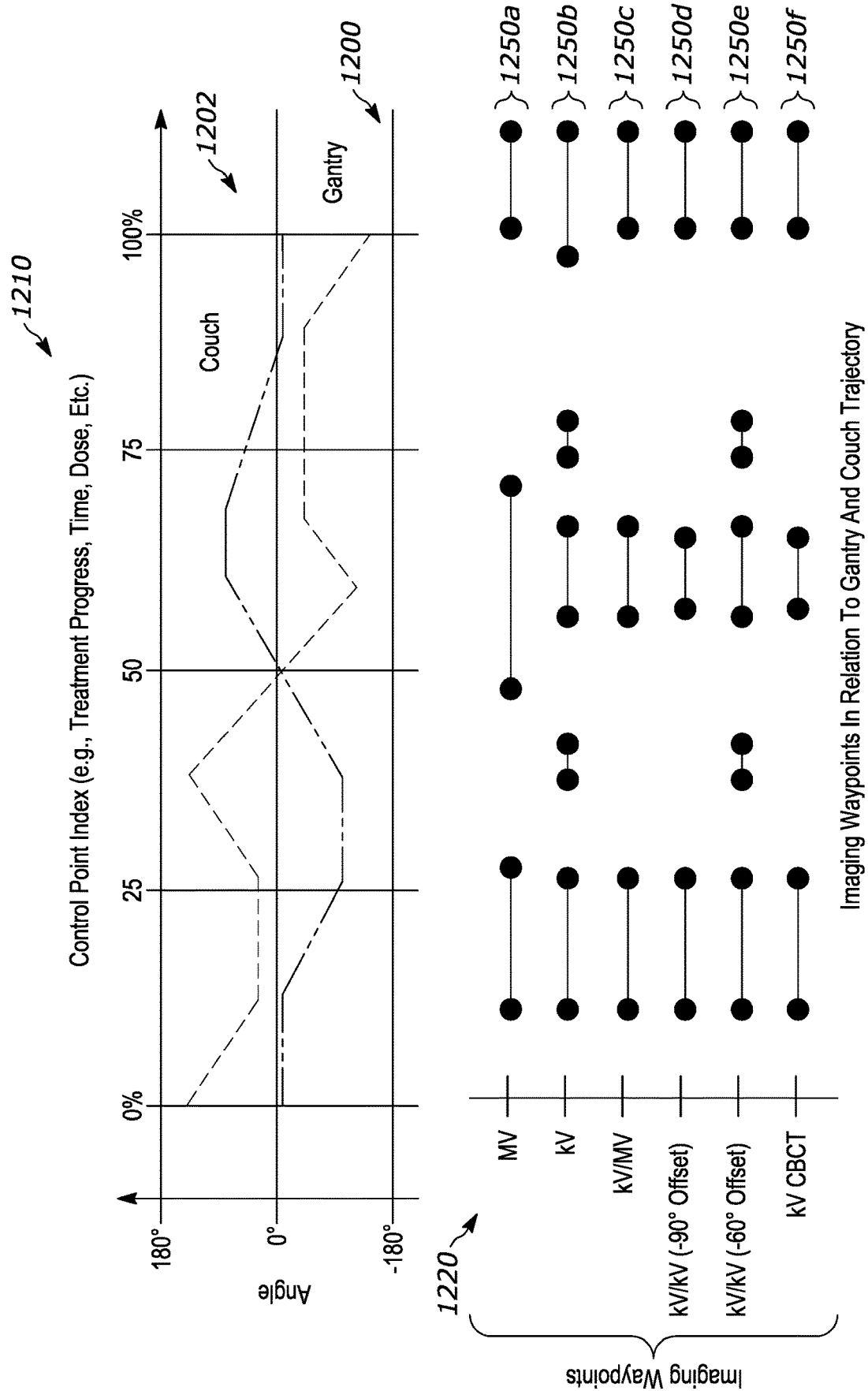
FIG. 12 illustrates imaging waypoints in relation to gantry and couch trajectory.

As shown in FIG. 12, the diagrams 1200, 1202 for both the gantry angle and the couch angle as the function of the control point index may be presented together in the same diagram 1210.

FIG. 12 also illustrates a diagram 1220 in relation to the diagram 1210. In particular, both diagrams 1210 and 1220 have the same x-axis, which represents control point index corresponding with treatment progress, time, dose, etc. The diagram 1200 is similar to that shown in FIG. 6A. As shown in FIG. 12, a first set 1250a of imaging waypoints is presented graphically for MV imaging, a second set 1250b of imaging waypoints is presented graphically for kV imaging, a third set 1250c of imaging waypoints is presented graphically for kV/MV imaging, a fourth set 1250d of imaging waypoints is presented graphically for kV/kV imaging in which the kV-imager positions are separated by 90°, a fifth set 1250e of imaging waypoints is presented graphically for kV/kV imaging in which the kV-imager positions are separated by 60°, and a sixth set 1250f of imaging waypoints is presented graphically for kV CBCT imaging. In other embodiments, the number of imaging offsets being presented graphically may be more than two, or fewer than two. As shown in the figure, the kV/MV imaging waypoints in the third set 1250c are obtained by filtering imaging waypoints that are common to both the first set 1250a and the second set 1250b.

Figure 13:
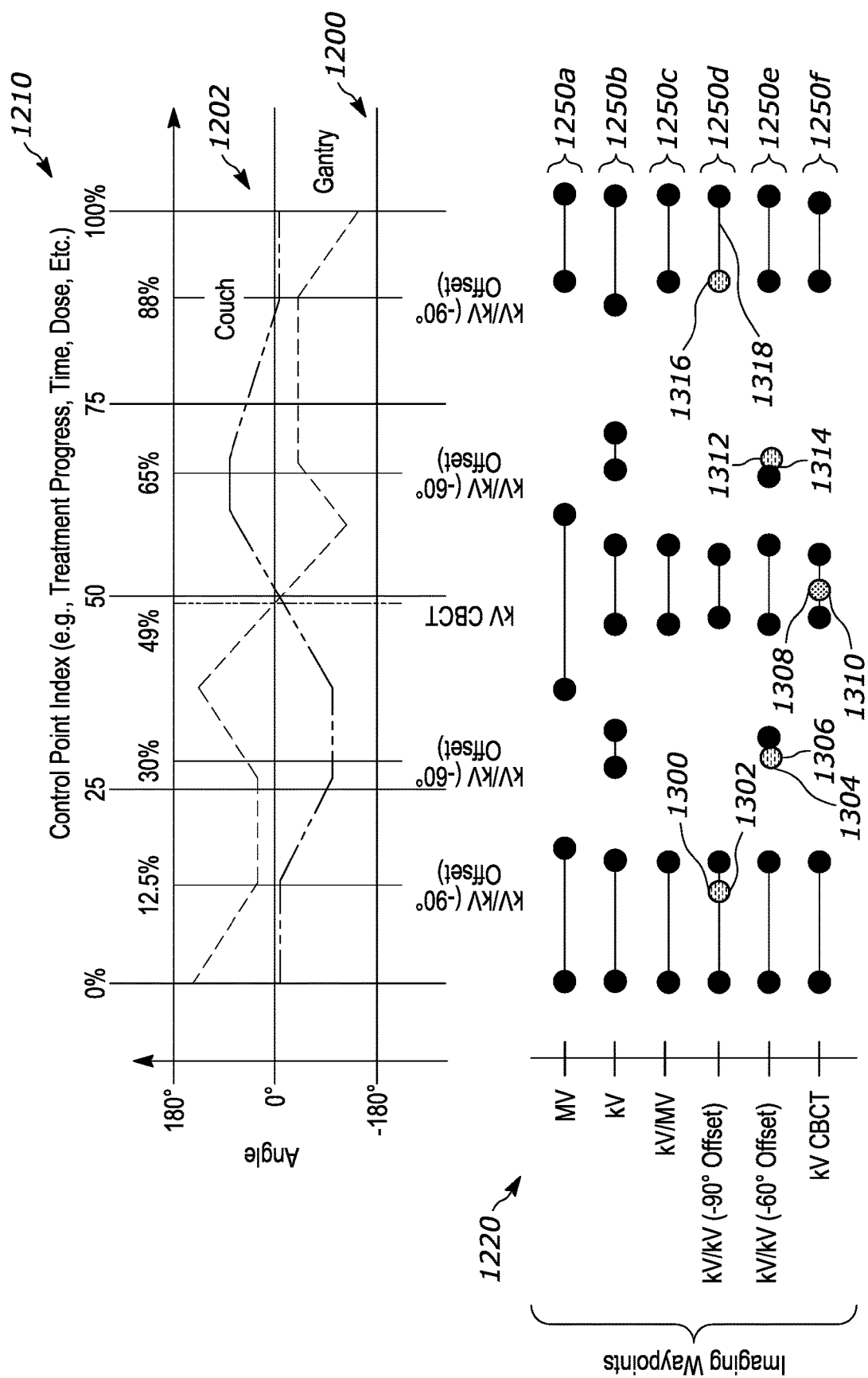
FIG. 13 illustrates imaging waypoints in relation to gantry and couch trajectory with used imaging waypoints.

FIG. 13 illustrates a selection 1300 of a subset 1302 of imaging waypoints in the fourth set 1250d for performing kV/kV imaging at 90° offset. As shown in the figure, the kV/kV imaging is prescribed by the selection 1300 to be performed when the gantry angle is 45° and when the couch angle is 0° (which will occur when the control point index is at 12.5%). FIG. 13 also illustrates a selection 1304 of a subset 1306 of imaging waypoints in the fifth set 1250e for performing kV/kV imaging at 60° offset. As shown in the figure, the kV/kV imaging is prescribed by the selection 1304 to be performed when the gantry angle is 60° and when the couch angle is −90° (which will occur when the control point index is at 30%). FIG. 13 also illustrates a selection 1308 of a subset 1310 of imaging waypoints in the sixth set 1250f for performing kV CBCT imaging. As shown in the figure, the kV CBCT imaging is prescribed by the selection 1308 to be performed when the gantry angle is 5° and when the couch angle is −5° (which will occur when the control point index is at 49%). FIG. 13 also illustrates a selection 1312 of a subset 1314 of imaging waypoints in the fifth set 1250e for performing kV/kV imaging at 60° offset. As shown in the figure, the kV/kV imaging is prescribed by the selection 1312 to be performed when the gantry angle is −45° and when the couch angle is 90° (which will occur when the control point index is at 65%). FIG. 13 also illustrates a selection 1316 of a subset 1318 of imaging waypoints in the fourth set 1250d for performing kV/kV imaging at 90° offset. As shown in the figure, the kV/kV imaging is prescribed by the selection 1316 to be performed when the gantry angle is −60° and when the couch angle is 0° (which will occur when the control point index is at 88%). The various selections of imaging arrangements (as selected using diagram 1220) may be presented in diagram 1210 in the form of vertical lines. In other embodiments, the selections may be presented using different graphics, such as line types, colors, etc.

In some embodiments, user interface 300 shown in FIG. 3 provided by the apparatus 200 shown in FIG. 2 may allow the user to modify one or more parameters (e.g., imaging geometry (such as source-to-imager distance, imaging distance, etc.), amount of imaging, machine geometry, etc.). In such cases, after the parameter(s) is modified, apparatus 200 will recalculate the imaging waypoints based on the modified parameter(s), and will present new graphics to present the recalculated imaging waypoints. In some cases, if the user is not satisfied with the current amount and types of imaging, the user can select an alternative amount of imaging presented by the apparatus 200, yielding a different (e.g., better) trajectory and dose distribution.

It should be noted that the types of imaging for which the imaging waypoints are presented are not limited to types based on energy (e.g., MV, kV, etc.), and types based on offset of imager positions (e.g., 90°, 60°, etc.). In some embodiments, the types of imaging for which imaging waypoints are presented may include room-based imaging (imaging using devices mounted to a room), gantry-based imaging (e.g., imaging involving imaging component(s) such as energy source, detector, or both, attached to a gantry), couch-based imaging (imaging involving imaging component(s) such as energy source, detector, or both, attached to a patient support), etc. Alternatively, or additionally, the types of imaging for which imaging waypoints are presented may include (1) imaging that allows a machine (e.g., gantry) to remain at a certain position (e.g., for room-based imaging, the gantry of the treatment machine may remain at a certain position while the room-based imaging device obtain image(s)), (2) imaging that requires a machine (e.g., gantry) to deviate from a certain position in order to obtain the image(s), (e.g., the gantry of the treatment machine may need to rotate for CBCT imaging, kV-kV imaging, MV-MV imaging, etc.), and/or (3) imaging that does not require an imaging component to move from a certain position. Accordingly, in some embodiments, the graphics of FIGS. 4-13 may include set(s) of imaging waypoints for any of these types of imaging.

Furthermore, it should be noted that the term "graphic", as used in this specification, is not limited to the examples shown in the figures, and that the term "graphic" may refer to other types of presentation or any information, such as numbers, texts, etc., which may represent waypoints, or may represent one or more solutions based on the waypoints.

In some embodiments, during treatment or on the day of treatment, the imaging waypoints selected during treatment planning for image acquisition may be presented to a user to indicate which machine geometry or treatment configuration allows imaging to take place. Through user interface 300, the user can see possible imaging waypoints determined previously during treatment planning. From the user interface, the user may see at which machine positions no images can be taken. In some cases, the user interface may also present all combination of source types and acquisition types in a timeline with respect to the imaging waypoints. Also, the user interface may present dose, beam trajectories, and/or machine geometries, with respect to the imaging waypoints. If desired, unused imaging waypoints may be enabled, or previously enabled imaging waypoints may be disabled at the treatment console. In some cases, the user interface may also allow the user to add imaging waypoints, and/or to remove imaging waypoints during treatment planning and/or during treatment.

In some embodiments, the apparatus 200 is configured to check that the previously proposed and selected imaging waypoints are valid (in terms of machine geometry and trajectories) on the day of the treatment. This is because the geometry of the treatment machine and its imaging components on the day of treatment may be different from those used during planning to determine the imaging waypoints. In one implementation, a surface scanner is used to scan the treatment machine and the patient on the day of treatment in order to verify the geometry of the machine and the geometry of the patient. Such may be performed during a treatment setup. If the surface scanner is not available, the actual geometry of the treatment machine on the day of treatment may be entered via user interface 300 of apparatus 200. Also, a previous surface model of the patient may be used, or a surface model extracted from an image (e.g., CT image) of the patient obtained on the day of the treatment may be used to represent the geometry of the patient. In some embodiments, the apparatus 200 may check the previously determined imaging waypoints by comparing the actual geometry of the treatment machine with the planned geometry of the treatment machine, and determining if the difference is within certain prescribed threshold(s). The apparatus 200 may also check the previously determined imaging waypoints by comparing the actual geometry of the patient with the planned geometry of the patient, and determining if the difference is within certain prescribed threshold(s). If the difference(s) is within the prescribed threshold(s), the apparatus 200 may then determine that the previously determined imaging waypoints are valid. Alternatively, the apparatus 200 may calculate new sets of imaging waypoints on the day of treatment using the actual geometry of the treatment machine, and the actual geometry of the patient, and determine whether the subset of imaging waypoints selected previously by the user from the imaging waypoints determined during planning still falls within the new sets of imaging waypoints. If the new sets of imaging waypoints determined on the day of treatment include all of the previously selected imaging waypoints, then the apparatus 200 may determine that the previously selected imaging waypoints are valid.

As discussed, the control point index may comprise or may represent gantry angles, couch angles, time points, doses, etc. Thus, in some embodiments, the imaging waypoints may be presented with respect to gantry angles, couch angles, time points, doses, etc. For example, the graphics presenting the imaging waypoints in FIGS. 4-13 may be done with respect to time. As another example, the graphics presenting the imaging waypoints in FIGS. 4-13 may be done with respect to planned accumulated dose (which increases over time). In other examples, the graphics presenting the imaging waypoints in FIGS. 4-13 may be done with respect to other parameters that vary temporally (over time).

Figure 14:
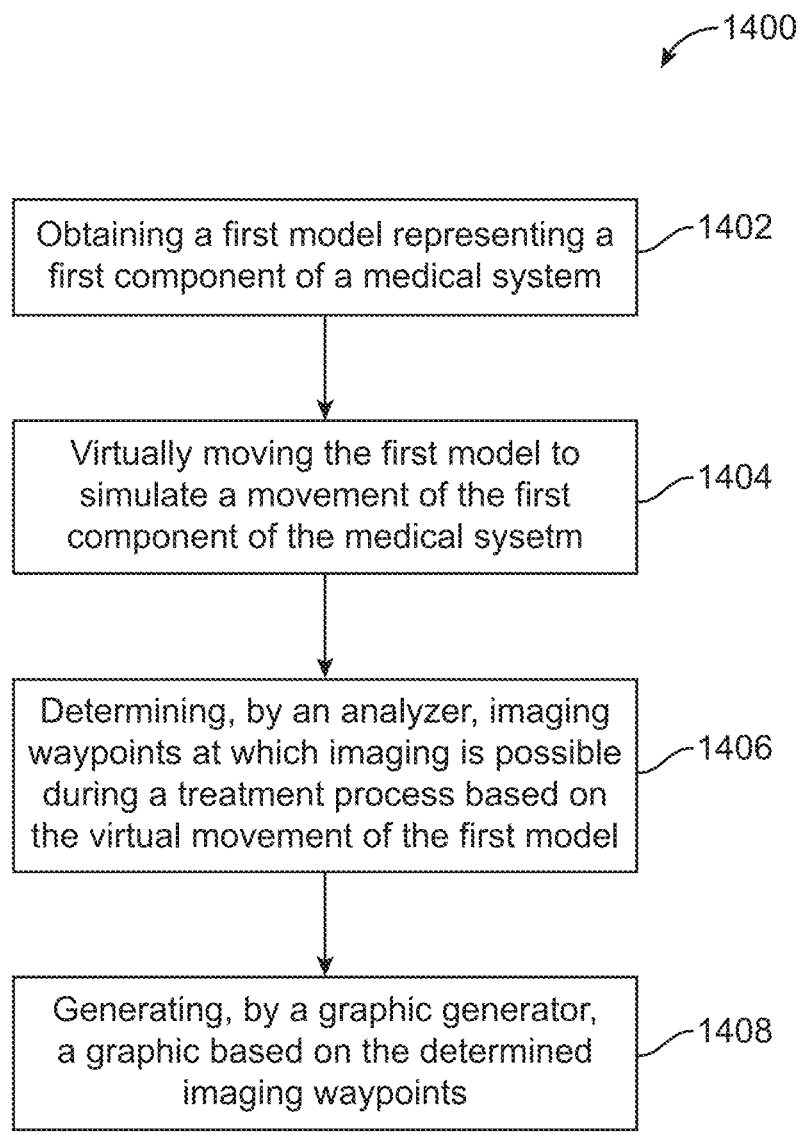
FIG. 14 illustrates a method according to some embodiments.

FIG. 14 illustrates a method 1400 for treatment planning and/or treatment setup in accordance with some embodiments. The method 1400 includes obtaining a first model representing a first component of a medical system (item 1402), virtually moving the first model to simulate a movement of the first component of the medical system (item 1404), determining, by an analyzer, imaging waypoints at which imaging is possible during a treatment process based on the virtual movement of the first model (item 1406), and generating, by a graphic generator, a graphic based on the determined imaging waypoints (item 1408).

In some embodiments, the method 1400 may also include obtaining, by the simulator, a second model representing a patient support, and virtually moving the second model, by the simulator, to simulate a movement of the patient support.

In some embodiments, the method 1400 may include obtaining, by the simulator, a surface model of a patient, and virtually moving the surface model, by the simulator, to simulate a movement of the patient due to a movement of a patient support In some embodiments, the method 1400 may include receiving, by an input, a user-defined amount of imaging coverage. In such cases, the analyzer may determine the imaging waypoints based on the user-defined amount of imaging coverage.

In some embodiments, the imaging waypoints comprise a first set of imaging waypoints and a second set of imaging waypoints. In such cases, the method 1400 may further include determining, by the analyzer, the first set of imaging waypoints for a first type of imaging, and to determine the second set of imaging waypoints for a second type of imaging. For example, the first type of imaging may comprise kV-imaging, and the second type of imaging may comprise MV-imaging.

In some embodiments, in the method 1400, a graphic may present the imaging waypoints as control point indices. By means of non-limiting examples, the control point indices comprise gantry angles, couch angles, time points, doses, etc.

In some embodiments, the imaging waypoints are arranged in a graphic as a function of imaging distance.

In some embodiments, the imaging distance and the imaging waypoints define one or more two-dimensional areas in a graphic.

In some embodiments, the imaging waypoints are arranged in a graphic as a function of angle offset between two kV-imager positions of a same imager or of different respective imagers. The imager may be a kV-imager, a MV-imager, or a hybrid imager that is capable of generating images using multiple energies (e.g., kV and MV images). Also, if there are multiple imagers, the imagers may be two kV-imagers, or a kV-imager and an MV-imager.

In some embodiments, the method 1400 may include determining, by the analyzer, gantry angle of a gantry associated with a treatment energy source as a function of control point index.

In some embodiments, the method 1400 may include providing a diagram, by the graphic generator, indicating the gantry angle as the function of the control point index.

In some embodiments, the method 1400 may include determining, by the analyzer, couch angle of a couch as a function of control point index.

In some embodiments, the method 1400 may include providing, by the graphic generator, a diagram indicating both the gantry angle and the couch angle as the function of the control point index.

In some embodiments, the method 1400 may include providing, by the graphic generator, a diagram indicating how the couch angle varies in relation to the gantry angle.

In some embodiments, the graphic provided by the graphic generator is a part of a user interface configured to allow a user to select one or more imaging arrangement(s) for a treatment plan.

In some embodiments, the method 1400 may be performed in response to a processing unit executing a set of instructions. Accordingly, in some embodiments, a product having a non-transitory medium storing a set of instructions may be provided. In such cases, an execution of the instructions by a processing unit will cause a method to be performed, the method comprising: obtaining a first model representing a first component of a medical system; virtually moving the first model to simulate a movement of the first component of the medical system; determining, by an analyzer, imaging waypoints at which imaging is possible during a treatment process based on the virtual movement of the first model; and generating, by a graphic generator, a graphic based on the determined imaging waypoints.

In some embodiments, the method 1400 may be performed once during treatment planning to inform a user what imaging options are possible while creating a treatment plan. During treatment planning, the method 1400 may be performed based on one or more planned machine geometries. Then the method 1400 may be performed again on the day of treatment—i.e., during treatment setup, to determine what imaging options are possible based on actual machine geometry. This may be performed to verify one or more planned imaging (if the method 1400 was previously performed during treatment planning), and/or to determine imaging options (e.g., if the method 1400 was not previously performed during treatment planning).

In one or more embodiments, the analyzer 204 may create imaging waypoints may associate the imaging waypoints with other parameters based on a specialized data structure. For example, the analyzer 204 may utilize a data structure that associate imaging waypoints with different types of imaging. The data structure may also associate imaging waypoints with different positions of the patient support, with different positions of the gantry, with different treatment progress, with different time, with different dose, etc., or any combination of the foregoing, using control point index as the common variable. In other embodiments, the data structure may associate control point indices with imaging waypoints, with different positions of the patient support, with different positions of the gantry, with different treatment progress, with different time, with different dose, etc., or any combination of the foregoing. The data structure may be stored in a non-transitory medium, and may be used later to create one or more graphics. For example, the graphic generator 206 may be a specialized processor in the sense that it may be configured to specifically process the unique data structure associating the various parameters in order to create the graphics (such as those illustrated in FIGS. 4A, 4B, 5A, 5B, 6A, 6B, and 7-13. The data structure is advantageous because it allows different diagrams to be created to assist a user in the development of a treatment plan while considering imaging options. In some cases, the data structure allows different diagrams to be created based on user's preference. For example, if the user wants to see imaging waypoints in relation with gantry angle, the graphic generator 206 may use the data structure (which associates imaging waypoints and gantry angle with the common variable—i.e., the control point index) to create a diagram illustrating a relationship between imaging waypoints and gantry angle.

The apparatus 200 and the method 1400 are advantageous because they provide a convenient way for a user to visualize imaging options during treatment planning. The user may readily see which type of imaging is available at different stages of a treatment to be executed. The apparatus 200 is also beneficial because it provides a user interface for a user to prescribe different types of imaging to be performed at different stages during a treatment. In some cases, the apparatus 200 may provide imaging waypoints as parameters for determining a treatment plan. For example, the apparatus 200 may output imaging waypoints (e.g., selected by a user for prescribing imaging to be performed) to a treatment planning system. The treatment planning system may then optimize a treatment plan utilizing the imaging waypoints as one of the optimization parameters. The resulting treatment plan will then include imaging consideration, and can be stored in a non-transitory medium for execution by a treatment system during treatment. Thus, the apparatus 200 and the method 1400 provide utility and tangible benefits in the medical field.

In one or more embodiments, described herein, the apparatus 200 may include a surface scanner for determining a surface model of a patient. The surface model may also include a surface of the patient support 14.

Although the apparatus 200 has been described as having a collision prediction system, in other embodiments, the apparatus 200 may not include any collision prediction system. In such cases, pre-calculated trajectories may be used by the apparatus 200 to determine imaging waypoints.

Also, the above embodiments have been described with reference to imaging waypoints representing temporal opportunities for imaging, in other embodiments, the technique described herein may be employed for other tasks that are different for imaging. For example, instead of imaging waypoints, the apparatus 200 may be configured to determine task waypoints indicating slot(s) or temporal point(s) (e.g., time) at which the performance of a task is possible.

Specialized Processing System

Figure 15:
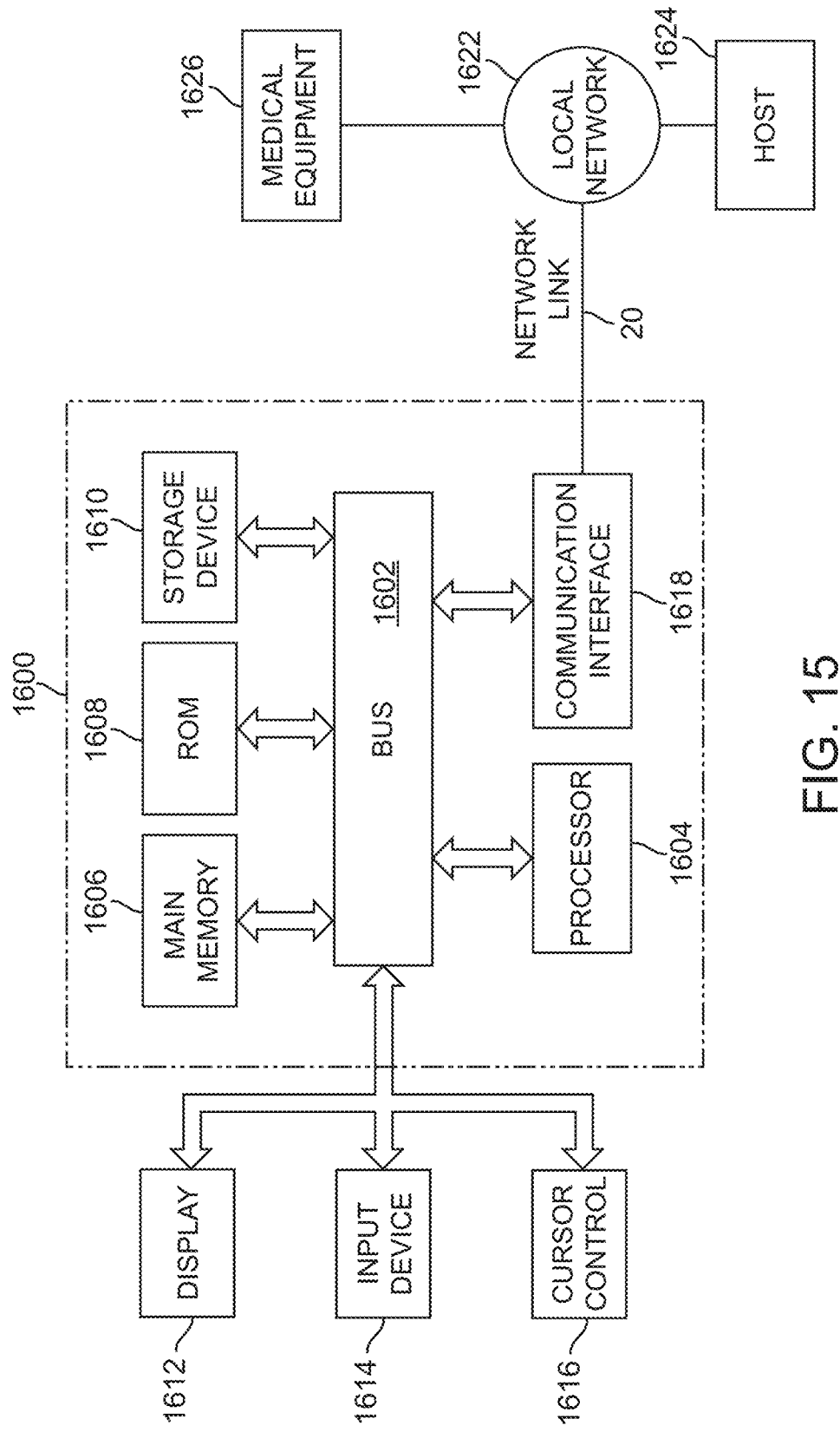
FIG. 15 illustrates a specialized processing system in accordance with some embodiments.

FIG. 15 is a block diagram illustrating an embodiment of a specialized processing system 1600 that can be used to implement various embodiments described herein. For example, the processing system 1600 may be configured to implement the method 1400 of FIG. 14 in accordance with some embodiments. Also, in some embodiments, the processing system 1600 may be used to implement the processing unit 200 of FIG. 2 and/or the processing unit 54 of FIG. 1. Processing system 1600 includes a bus 1602 or other communication mechanism for communicating information, and a processor 1604 coupled with the bus 1602 for processing information. The processor 1604 may be an example of the processor 54 of FIG. 1A, an example of the processor 80 of FIG. 1B/1C, or an example of any processor described herein. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processor system 1600 may be coupled via the bus 1602 to a display 167, such as a flat panel, for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the processing system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. An apparatus for treatment planning and/or for treatment setup, comprising:
at least one processor and memory comprising executable instructions that cause the at least one processor to;
obtain a first model representing a first component of a medical system, and virtually move the first model to simulate a treatment movement of the first component of the medical system, wherein the treatment movement corresponds to movement of the first component to deliver treatment radiation to a target tissue;
receive, via an input user interface, one or more user-defined parameters comprising a user-defined amount of imaging coverage and a user-defined imaging source type, wherein the amount of imaging coverage corresponds to an amount of imaging to be performed relative to the delivery of the treatment radiation;
determine imaging waypoints based on the virtual movement of the first model and on the one or more user-defined imaging parameters, wherein the imaging waypoints indicate imaging opportunities to perform imaging during the treatment movement; and
generate a graphic user interface displaying the determined imaging waypoints before the imaging is performed, wherein the determined imaging waypoints are selectable in the graphic user interface.

2. The apparatus of claim 1, wherein the executable instructions also cause the at least one processor to obtain a second model representing a patient support, and virtually move the second model to simulate a movement of the patient support; wherein the determination of the imaging waypoints is further based on the virtual movement of the second model.

3. The apparatus of claim 1, wherein the executable instructions also cause the at least one processor to obtain a surface model of a patient, and virtually move the surface model to simulate a movement of the patient due to a movement of a patient support.

4. The apparatus of claim 1, wherein the executable instructions also cause the at least one processor to determine a set of system configurations which do not result in a collision of the first component with another component of the medical system.

5. The apparatus of claim 1, wherein the imaging waypoints comprise a first set of imaging waypoints and a second set of imaging waypoints, and wherein the analyzer is configured to determine the first set of imaging waypoints for a first type of imaging, and to determine the second set of imaging waypoints for a second type of imaging.

6. The apparatus of claim 5, wherein the first type of imaging comprises kV-imaging, and the second type of imaging comprises MV-imaging.

7. The apparatus of claim 5, wherein the first type of imaging is room-based imaging, gantry-based imaging, or couch-based imaging.

8. The apparatus of claim 1, wherein the graphic user interface presents the imaging waypoints as control point indices, wherein the control point indices comprise or represent: gantry angles, couch angles, time points, or doses.

9. The apparatus of claim 1, wherein the graphic user interface shows the imaging waypoints in relation with different imaging distances.

10. The apparatus of claim 9, wherein the imaging distance and the imaging waypoints define one or more two-dimensional areas in the graphic user interface.

11. The apparatus of claim 1, wherein the graphic user interface shows the imaging waypoints in relation with different angle offsets between two kV-imager positions of a same imager or of different respective imagers.

12. The apparatus of claim 1, wherein the executable instructions also cause the processor to determine a gantry angle of a gantry associated with a treatment energy source as a function of control point index.

13. The apparatus of claim 12, wherein the executable instructions also cause the at least one processor to provide a diagram indicating the gantry angle as the function of the control point index.

14. The apparatus of claim 12, wherein the executable instructions also cause the at least one processor to determine a couch angle of a couch as a function of control point index.

15. The apparatus of claim 14, wherein the executable instructions also cause the at least one processor to provide a diagram indicating both the gantry angle and the couch angle as the function of the control point index.

16. The apparatus of claim 14, wherein the executable instructions also cause the at least one processor to provide a diagram indicating how the couch angle varies in relation to the gantry angle.

17. The apparatus of claim 1, wherein the graphic user interface is configured to allow a user to select one or more imaging arrangement(s) for a treatment plan.

18. The apparatus of claim 1, wherein the graphic user interface shows the imaging waypoints in relation with different source-to-imager distances (SIDs).

19. The apparatus of claim 1, wherein the imaging waypoints indicate the imaging opportunities to allow a user of the apparatus to selectively decide whether to prescribe the imaging.

20. The apparatus of claim 1, wherein the determined imaging waypoints comprise imaging waypoints that does not require the first component of the medical system to move to perform imaging.

21. A method for treatment planning and/or for treatment setup, comprising:
   obtaining a first model representing a first component of a medical system;
   virtually moving the first model to simulate a treatment movement of the first component of the medical system, wherein the treatment movement corresponds to movement of the first component to deliver treatment radiation to a target tissue;
   obtaining, via an input user interface, one or more user-defined parameters comprising a user-defined amount of imaging coverage and a user-defined imaging source type, wherein the amount of imaging coverage corresponds to an amount of imaging to be performed relative to the delivery of the treatment radiation;
   determining imaging waypoints based on the virtual movement of the first model and on one or more user-defined imaging parameters, wherein the imaging waypoints indicate imaging opportunities to perform imaging during the treatment movement; and
   generating a graphic user interface displaying the determined imaging waypoints before the imaging is performed, wherein the determined imaging waypoints are selectable in the graphic user interface.

22. A product having a non-transitory medium storing a set of instructions, an execution of which by a processing unit causes a method to be performed during treatment planning and/or treatment setup, the method comprising:
   obtaining a first model representing a first component of a medical system;
   virtually moving the first model to simulate a treatment movement of the first component of the medical system, wherein the treatment movement corresponds to movement of the first component to deliver treatment radiation to a target tissue;
   obtaining, via an input user interface, one or more user-defined parameters comprising a user-defined amount of imaging coverage and a user-defined imaging source type, wherein the amount of imaging coverage corresponds to an amount of imaging to be performed relative to the delivery of the treatment radiation;
   determining imaging waypoints based on the virtual movement of the first model and on one or more user-defined imaging parameters, wherein the imaging waypoints indicate imaging opportunities to perform imaging during the treatment movement; and
   generating a graphic user interface displaying the determined imaging waypoints before the imaging is performed, wherein the determined imaging waypoints are selectable in the graphic user interface.

* * * * *